United States Patent [19]
Ye et al.

[11] Patent Number: 6,120,993
[45] Date of Patent: Sep. 19, 2000

[54] 5-OXOPROLINASE

[75] Inventors: Guo-jie Ye, Chicago, Ill.; Esther Breslow, Englewood, N.J.; Alton Meister, deceased, late of New York, N.Y.; by Kenneth Meister, executor, Wilton, Conn.

[73] Assignee: Cornell Research Foundation, Inc., Ithaca, N.Y.

[21] Appl. No.: 08/762,428

[22] Filed: Dec. 9, 1996

[51] Int. Cl.[7] .............................. C12Q 1/68; C12N 15/11; C12N 15/85; C07H 21/04

[52] U.S. Cl. .......................... 435/6; 435/69.1; 435/91.31; 435/325; 435/352; 435/320.1; 536/23.1; 536/23.2; 536/23.5; 536/24.3; 536/24.31; 536/24.5

[58] Field of Search ...................... 435/6, 69.1, 91.31, 435/325, 352, 320.1, 455; 536/23.1, 23.2, 23.5, 24.3, 24.31, 24.5; 514/44

[56] References Cited

U.S. PATENT DOCUMENTS 5,585,479 12/1996 Hoke et al. ............................... 536/24.5

OTHER PUBLICATIONS

Burke, J. Clearing the Way for Ribozymes. Nature Biotechnology vol. 15:414, May 1997.

Chen et al. Efficient Hammerhead Ribozyme and Antisense RNA Targeting in a Slow Ribosome *Eschericia coli* Mutant. Nature Biotechnology vol. 15:432–436, May 1997.

Bennet, F. Antisense Research. Science vol.271:434, Jan. 26, 1996.

Orkin et al. Report and Recommendations of the Panel to Assess the NIH Investment in Research on Gene Therapy, Dec. 7, 1995.

Hillier et al. Databases EST–STS and EST–STS–TWO on MPSRCH Accession number H38090, Sep. 16, 1996.

Gipp et al., "Cloning and Sequencing of the cDNA for the Light Subunit of Human Liver γ–Glutamylcysteine Synthetase and Relative mRNA Levels for Heavy and Light Subunits in Human Normal Tissues," Biochemical and Biophysical Research Communications 206:584–589 (1995).

Kim et al., "Amidohydrolysis of N–Methylhydantion Coupled with ATP Hydrolysis," Biochemical and Biophysical Research Communications 142:1006–1912 (1987).

LaPointe et al., "Cloning, Sequencing, and Expression in *Eschericia coli* of the D–Hydantoinase Gene from *Pseudomonas putida* and Distribution of Homologous Genes in Other Microorganisms," Applied and Environmental Microbiology 60:888–895 (1994).

Meister et al., "5–Oxo–L–prolinase from Rat Kidney," Methods in Enzymology 113:445–451 (1985).

Seddon et al., "5–Oxo–L–prolinase from *Pseudomonas putida*," Methods in Enzymology 113:451–458 (1985).

Seddon et al., "Resolution of 5–Oxo–L–prolinase into a 5–Oxo–L–proline–dependent ATPase and a Coupling Protein," Journal of Biological Chemistry 259:8091–8094 (1984).

Tzermia et al., "The Complete Sequencing of a 24.6 kb Segment of Yeast Chromosome XI Identified the Known Loci URA1, SAC1 and TRP3, and Revealed 6 New Open Reading Frames Including Homologues to the Threonine Dehydratases, Membrane Transporters, Hydantoinases and the Phospholipase $A_2$–Activating Protein," Yeast 10:663–679 (1994).

Van Der Werf and Meister, "Isolation of 5–Oxoprolinase from a Prokaryote," Biochemical and Biophysical Research Communications 56:90–96 (1974).

Watabe et al., "Cloning and Sequecing of the Genes Involved in the Conversion of 5–Substituted Hydantoins to the Corresponding L Amino Acids from the Native Plasmid of Pseudomonas sp. Strain NS671," Journal of Bacteriology 174:962–969 (1992).

Williamson and Meister, "Effect of Sulfhydryl Group Modification on the Activities of 5–Oxo–L–prolinase," Journal of Biological Chemistry 257:9161–9172 (1982).

Yamashiro et al., "Mechanism of Stereospecific Production of L–Amino Acids from the Corresponding 5–Substituted Hydantoins by *Bacillus brevis*," Agric Biol Chem 52:2857–2863 (1988).

*Primary Examiner*—John S. Brusca
*Assistant Examiner*—Sean McGarry
*Attorney, Agent, or Firm*—Nixon Peabody LLP

[57] ABSTRACT

The present invention is directed to isolated nucleic acid molecules encoding mammalian 5-oxoprolinase (m 5-OPase). Expression vectors and host cells comprising the nucleic acid molecules are also provided, as well as methods for increasing or decreasing the expression of m 5-OPase in host cells. The invention further provides a method of screening a substance for the ability of the substance to modify m 5-OPase function, and a method for isolating other m 5-OPase molecules. DNA oligomers and antibodies specific for m 5-OPase are provided, each of which can be used to detect m 5-OPase in a sample.

22 Claims, 1 Drawing Sheet

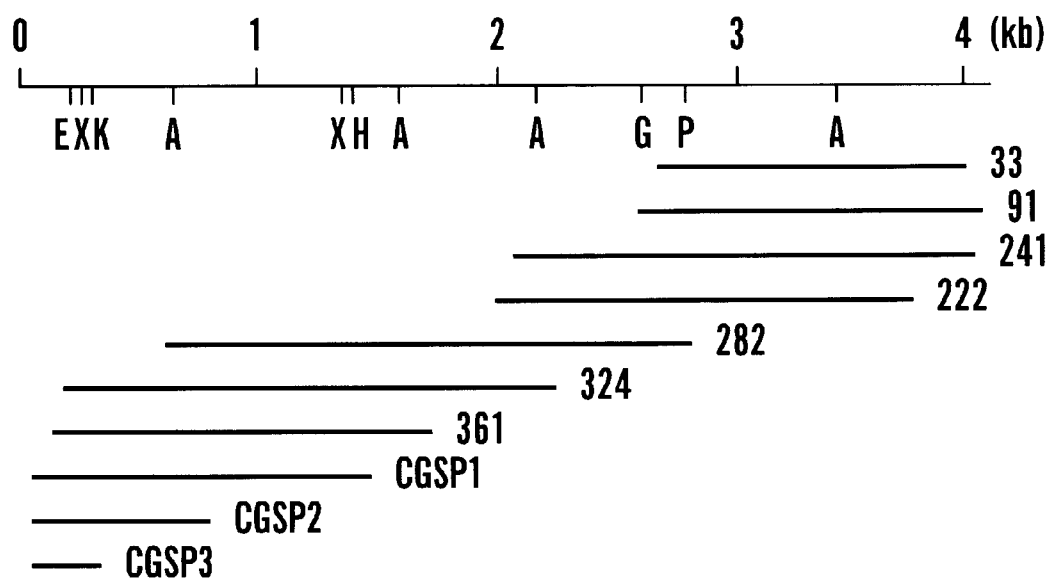

5-OXOPROLINASE

The subject matter of this application was made with support from the United States Government under grant DK-12034 of the National Institutes of Health.

FIELD OF THE INVENTION

The present invention relates generally to the enzyme mammalian 5-oxoprolinase, and more particularly to nucleic acid molecules encoding mammalian 5-oxoprolinase and uses thereof.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The tripeptide thiol glutathione (L-γ-glutamyl-L-cysteinylglycine; GSH) is found within virtually all cells. It functions in metabolism, transport, and cellular protection. Specifically, for example, glutathione participates in transhydrogenation reactions that are involved in the formation and maintenance of the sulfhydryl group of other molecules (e.g., coenzyme A, various enzymes, and other proteins). Glutathione provides reducing capacity for various reactions, e.g., the formation of deoxyribonucleotides by ribonucleotide reductase. Glutathione also functions in the detoxification of hydrogen peroxide, other peroxides, and free radicals. In addition, glutathione plays a role in detoxification of a variety of foreign compounds which interact with glutathione and which are ultimately excreted in the form of mercapturic acids. Analogous derivatives of glutathione are formed with endogenous metabolites, e.g., in the metabolism of leukotrienes, prostaglandins, steroids, and melanins. There is also evidence that the γ-glutamyl moiety of glutathione functions in the transport of amino acids (especially cysteine and certain neutral amino acids) and possibly also of peptides and amines.

Glutathione synthesis takes place within almost all animal cells and in those of many plants and microorganisms. Two enzymes required for the synthesis of this tripeptide from L-glutamate (γ-glutamylcysteine synthetase and glutathione synthetase) have been isolated from a number of different sources (Dolphin et al. 1989; Snoke and Bloch 1952; Snoke 1955; Meister 1974).

Gamma-glutamylcysteine (γ-glu-cys) synthetase catalyzes the rate-limiting step of GSH synthesis:

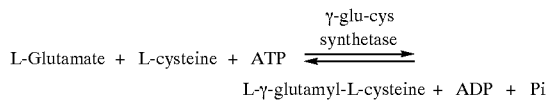

Gamma-glutamylcysteine is feedback inhibited by GSH (Richman and Meister 1975; Huang et al. 1993).

Glutathione synthetase catalyzes the synthesis of GSH from γ-glutamylcysteine and glycine:

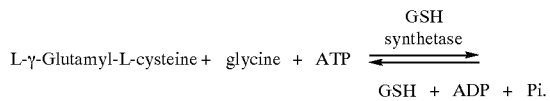

5-Oxo-L-prolinase(5-OPase) catalyzes the ATP-dependent cleavage of 5-oxoproline to L-glutamate:

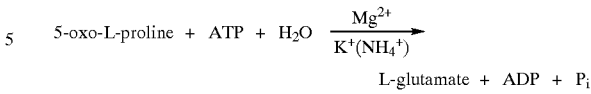

Glutathione synthetase deficiency in humans is associated with potentially serious health complications. Two general types of such deficiency have been observed (Meister and Larsson 1995). In one, an unstable form of GSH synthetase is expressed, leading to an apparently selective deficiency of GSH in the erythrocyte. In 5-oxoprolinuria, the result of another type of GSH synthetase deficiency, dramatic and potentially fatal metabolic consequences occur as a result of over-production of 5-oxoproline which leads to severe metabolic acidosis. In this condition, there is over-production of γ-glutamylcysteine, whose synthesis is not feedback inhibited because of the low levels of GSH and possibly because there is induction of γ-glutamylcysteine synthetase. γ-Glutamylcysteine is converted by the action of γ-glutamylcyclotransferase to cysteine and 5-oxoproline. Cysteine is used by γ-glutamylcysteine synthetase (in a futile cycle), and 5-oxoproline accumulates in amounts that exceed the capacity of 5-oxoprolinase to convert it to glutamate. This leads to substantial accumulation of 5-oxoproline and to its urinary excretion in amounts that may be as high as 30 grams per day (normally <0.14 g. per day) (Meister and Larsson 1995). Severe damage to the central nervous system, and even potentially death, are among the potential complications. There are also recent reports of another form of 5-oxoprolinuria, associated with a deficiency of 5-oxoprolinase.

Modifications of glutathione metabolism are sometimes desirable even in persons having normal glutathione levels. Such modifications may be achieved by administration of selective enzyme inhibitors to decrease intracellular glutathione levels, or by providing compounds that increase glutathione synthesis. Such effects are potentially useful, respectively, in chemotherapy and radiation therapy, and in protecting cells against the toxic effects of drugs, other foreign compounds and oxygen.

Modification of GSH metabolism to deplete or increase cellular GSH may serve various purposes. For instance, it has long been known that thiols protect cells against the effects of irradiation. Since decreasing cellular GSH makes cells more susceptible to irradiation, glutathione depletion is useful in chemotherapeutic situations in which the cells to be killed and the cells to be spared have substantially different quantitative requirements for GSH. Depletion of GSH by inhibition of its synthesis also serves as a valuable adjuvant in chemotherapy with drugs that are detoxified by reactions involving GSH.

Conversely, development of resistance to a drug or to radiation may be associated with an increase in cellular GSH. GSH serves effectively in the detoxification of many drugs, and it is known that a significant pathway of acetaminophen detoxification involves conjugation with GSH.

Treatment with a thiazolidine such as L-2-oxothiazolidine-4-carboxylic acid, may be of value to patients with liver disease and to premature infants who may be deficient in the utilization of methionine sulfur for cysteine formation, and thus in GSH synthesis. The effectiveness of such a thiazolidine as an intracellular cysteine precursor depends on the presence of 5-oxoprolinase, an enzyme activity found in almost all animal cells.

The cleavage of 5-oxoproline by 5-OPase to glutamate is highly unusual in that hydrolysis of ATP is required for the cleavage of a specific peptide bond (Meister et al. 1985). 5-OPase has been found in mammalian tissues (Van Der Werf et al. 1971), plants (Mazelis and Creveling 1978), and microorganisms (Van Der Werf and Meister 1974; Mooz and Wigglesworth 1976). Apparently homogeneous preparations of 5-OPase from rat kidney (Williamson and Meister 1982) and *Pseudomonas putida* (Seddon et al. 1984) have been obtained and were used for physical characterization and for studies of catalytic mechanism. 5-OPase from rat kidney is composed of two apparently identical subunits which exhibit a molecular mass of 142,000 Da on SDS-polyacrylamide gel electrophoresis (Williamson and Meister 1982). The enzyme is evidently a "sulfhydryl enzyme" (Van Der Werf et al. 1975) and has a number of sulfhydryl groups/monomer (Williamson and Meister 1982). The relationship between the essential sulfhydryl groups of the enzyme and its various catalytic activities has been probed (Williamson and Meister 1982). Unlike rat kidney 5-OPase, *Pseudomonas putida* 5-OPase is composed of two different, reversibly dissociable protein components, A and B (Seddon et al. 1984). Component A catalyzes an initial step in the reaction that involves 5-oxoproline and ATP (Seddon and Meister 1986). Component B may function as a catalyst that converts a phosphorylated form of 5-oxoproline to glutamate, or it might alter the conformation of Component A so as to facilitate the reaction (Li et al. 1988; Li et al. 1989).

Data are lacking, however, on the amino acid sequence of the 5-oxoprolinase enzyme from any mammalian source. Knowledge of the amino acid sequence of the enzyme and the cloning of the encoding cDNA are essential for further studies on the structure, mechanism of action, and physiological function of the enzyme.

A need continues to exist for the determination of the nucleotide and amino acid sequences of mammalian 5-oxoprolinase.

SUMMARY OF INVENTION

To this end, the subject invention provides an isolated nucleic acid molecule encoding a mammalian 5-oxoprolinase. In one embodiment, the nucleic acid molecule encodes a rat 5-oxoprolinase. The invention also provides an antisense nucleic acid molecule complementary to at least a portion of the mRNA encoding the mammalian 5-oxoprolinase.

The isolated nucleic acid molecules of the invention can be inserted into suitable expression vectors and/or host cells. Expression of the nucleic acid molecules encoding the mammalian 5-oxoprolinase results in production of mammalian 5-oxoprolinase in a host cell. Expression of the antisense nucleic acid molecules in a host cell results in decreased expression of the mammalian 5-oxoprolinase.

The invention further provides a ribozyme having a recognition sequence complementary to a portion of mRNA encoding a mammalian 5-oxoprolinase. The ribozyme can be introduced into a cell to also achieve decreased expression of mammalian 5-oxoprolinase in the cell.

The invention further provides a method of screening a substance for the ability of the substance to modify 5-oxoprolinase function, and a method of obtaining DNA encoding a mammalian 5-oxoprolinase.

Further provided is an isolated nucleic acid molecule encoding a mammalian 5-oxoprolinase, wherein the nucleic acid molecule encodes a first amino acid sequence having at least 90% amino acid identity to a second amino acid sequence. The second amino acid sequence has a sequence as shown in SEQ ID NO:6.

The invention further provides a DNA oligomer capable of hybridizing to a nucleic acid molecule encoding a mammalian 5-oxoprolinase. The DNA oligomer can be used in a method of detecting presence of a mammalian 5-oxoprolinase in a sample, which method is also provided by the subject invention. The invention also provides an antibody or fragment thereof specific for the mammalian 5-oxoprolinase encoded by the nucleic acid molecule of the subject invention. The antibody or fragment thereof can also be used in a method of detecting the presence of a mammalian 5-oxoprolinase in a sample, which method is also provided by the subject invention.

The invention also provides a plasmid designated pRO-PASE and deposited with the American Type Culture Collection under Accession No. 98272, as well as an NdeI/SalI restriction fragment of about 4.0 kb from the plasmid designated pROPASE.

BRIEF DESCRIPTION OF THE DRAWING

These and other features and advantages of this invention will be evident from the following detailed description of preferred embodiments when read in conjunction with the accompanying drawing in which:

FIG. 1 illustrates the restriction map and overlapping rat kidney 5-oxoprolinase cDNA clones.

DETAILED DESCRIPTION

The plasmid designated pROPASE has been deposited in the *Escherichia coli* strain designated pROPASE pursuant to, and in satisfaction of, the requirements of the Budapest Treaty on the International Recognition of the Deposit of Microorganisms for the Purposes of Patent Procedure, with the American Type Culture Collection (ATCC), 10801 University Boulevard, Manassas, Va. 20110-2209 under ATCC Accession No. 98272 on Dec. 6, 1996.

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized or recombinantly produced nucleic acid molecules).

As further used herein, the terms "corresponding to" when used in conjunction with a SEQ ID NO for a nucleotide sequence refer to a nucleotide sequence which is substantially the same nucleotide sequence, or derivatives or equivalents thereof (such as deletion and hybrid variants thereof, splice variants thereof, etc.), which retain the function of the 5-oxoprolinase enzyme. Nucleotide additions, deletions, and/or substitutions, such as those which do not affect the translation of the DNA molecule, are within the scope of a nucleotide sequence corresponding to or having or as shown in or consisting of a particular nucleotide sequence (i.e. the amino acid sequence encoded thereby remains the same). Such additions, deletions, and/or substitutions can be, for example, the result of point mutations made according to methods known to those skilled in the art. It is also possible to substitute a nucleotide which alters the amino acid sequence encoded thereby, where the amino acid substituted is a conservative substitution or where amino acid homology is conserved, and where the function as a 5-oxoprolinase enzyme is retained. It is also possible to have minor nucleotide additions, deletions, and/or substitutions which do not alter the function of the resulting 5-oxoprolinase.

Similarly, the term "corresponding to" when used in conjunction with a SEQ ID NO for an amino acid sequence refers to an amino acid sequence which is substantially the same amino acid sequence or derivatives thereof. Amino acid additions, deletions, and/or substitutions which do not negate the ability of the resulting protein to form a functional 5-oxoprolinase are within the scope of an amino acid sequence corresponding to or having or as shown in or consisting of a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, proline, alanine, glycine, serine, and threonine, all of which are neutral, weakly hydrophobic residues, are of the same type. Glutamine, glutamic acid, asparagine, and aspartic acid, all of which are hydrophilic residues, are of the same type. Another type of residue is the basic, hydrophilic amino acid residue, which includes histidine, lysine, and arginine. Leucine, isoleucine, valine, and methionine, all of which are hydrophobic, aliphatic amino acid residues, form yet another type of residue. Yet another type of residue consists of phenylalanine, tyrosine, and tryptophan, all of which are hydrophobic, aromatic residues. Further descriptions of the concept of conservative substitutions are given by French and Robson 1983, Taylor 1986, and Bordo and Argos 1991.

As further used herein, the term "corresponding to" when used in conjunction with a SEQ ID NO for a nucleotide or amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified nucleotide or amino acids within the recited sequence. For example, those skilled in the art will readily understand than an adenine nucleotide could be replaced with a methyladenine, or a cytosine nucleotide could be replaced with a methylcytosine, if a methyl side chain is desirable. Nucleotide sequences having a given SEQ ID NO are intended to encompass nucleotide sequences containing these and like derivative or modified nucleotides, as well as cyclic variations, which retain the function of a 5-oxoprolinase enzyme. As a further example, those skilled in the art will readily understand that an asparagine residue could be replaced with an ethylasparagine if an ethyl side chain is desired, a lysine residue could be replaced with a hydroxylysine if an OH side chain is desired, or a valine residue could be replaced with a methylvaline if an additional methyl side chain is desired. Amino acid sequences having a given SEQ ID NO are intended to encompass amino acid sequences containing these and like derivative or modified amino acids, as well as cyclic variations, where the function of 5-oxoprolinase is retained. Cyclic, as used herein, also refers to cyclic versions of the derivative or modified nucleotides and amino acids.

With these definitions in mind, the subject invention provides an isolated nucleic acid molecule encoding a mammalian 5-oxoprolinase (m 5-OPase). The nucleic acid molecule can be deoxyribonucleic acid (DNA) or ribonucleic acid (RNA, including messenger RNA or mRNA), genomic or recombinant, biologically isolated or synthetic.

The DNA molecule can be a cDNA molecule, which is a DNA copy of a messenger RNA (mRNA) encoding the m 5-OPase.

In one embodiment, the m 5-OPase is a rat 5-oxoprolinase. An example of such a rat 5-oxoprolinase is the 5-OPase encoded by the nucleotide sequence as shown in SEQ ID NO:5. The amino acid sequence encoded by this nucleotide sequence is shown in SEQ ID NO:6.

The invention also provides an antisense nucleic acid molecule that is complementary to at least a portion of the mRNA encoding the m 5-OPase. Antisense nucleic acid molecules can be RNA or single-stranded DNA, and can be complementary to the entire mRNA molecule encoding the m 5-OPase (i.e. of the same nucleotide length as the entire molecule). It may be desirable, however, to work with a shorter molecule. In this instance, the antisense molecule can be complementary to a portion of the entire mRNA molecule encoding the m 5-OPase. These shorter antisense molecules are capable of hybridizing to the mRNA encoding the entire molecule, and preferably consist of at least twenty nucleotides. These antisense molecules can be used to reduce levels of m 5-OPase, by introducing into cells an RNA or single-stranded DNA molecule that is complementary to at least a portion of the mRNA of the m 5-OPase (i.e. by introducing an antisense molecule). The antisense molecule can base-pair with the mRNA of the m 5-OPase, preventing translation of the mRNA into protein. Thus, an antisense molecule to the m 5-OPase can prevent translation of mRNA encoding the m 5-OPase into a functional m 5-OPase protein.

More particularly, an antisense molecule complementary to at least a portion of mRNA encoding a m 5-OPase can be used to decrease expression of a functional m 5-OPase. A cell with a first level of expression of a functional m 5-OPase is selected, and then the antisense molecule is introduced into the cell. The antisense molecule blocks expression of functional m 5-OPase, resulting in a second level of expression of a functional m 5-OPase in the cell. The second level is less than the initial first level.

Antisense molecules can be introduced into cells by any suitable means. In one embodiment, the antisense RNA molecule is injected directly into the cellular cytoplasm, where the RNA interferes with translation. A vector may also be used for introduction of the antisense molecule into a cell. Such vectors include various plasmid and viral vectors. For a general discussion of antisense molecules and their use, see Han et al. 1991 and Rossi 1995.

The invention further provides a special category of antisense RNA molecules, known as ribozymes, having recognition sequences complementary to specific regions of the mRNA encoding the m 5-OPase. Ribozymes not only complex with target sequences via complementary antisense sequences but also catalyze the hydrolysis, or cleavage, of the template mRNA molecule.

Expression of a ribozyme in a cell can inhibit gene expression (such as the expression of a m 5-OPase). More particularly, a ribozyme having a recognition sequence complementary to a region of a mRNA encoding a m 5-OPase can be used to decrease expression of m 5-OPase. A cell with a first level of expression of m 5-OPase is selected, and then the ribozyme is introduced into the cell. The ribozyme in the cell decreases expression of m 5-OPase in the cell, because mRNA encoding the m 5-OPase is cleaved and cannot be translated.

Ribozymes can be introduced into cells by any suitable means. In one embodiment, the ribozyme is injected directly into the cellular cytoplasm, where the ribozyme cleaves the mRNA and thereby interferes with translation. A vector may be used for introduction of the ribozyme into a cell. Such vectors include various plasmid and viral vectors (note that the DNA encoding the ribozyme does not need to be "incorporated" into the genome of the host cell; it could be expressed in a host cell infected by a viral vector, with the vector expressing the ribozyme, for instance). For a general discussion of ribozymes and their use, see Sarver et al. 1990, Chrisey et al. 1991, Rossi et al. 1992, and Christoffersen et al. 1995.

The nucleic acid molecules of the subject invention can be expressed in suitable host cells using conventional techniques. Any suitable host and/or vector system can be used to express the m 5-OPase. For in vitro expression, bacterial hosts (for example, *Escherichia coli*) and mammalian hosts (for example, Hela cells, Cv-1 cells, COS cells) are preferred. For in vivo expression, the most suitable host cell depends on the goal of the expression. For example, in cells of a subject afflicted with 5-oxoprolinuria it is desirable to increase expression of m 5-OPase so that the m 5-OPase cleaves the excess 5-oxoproline forming L-glutamate. In cells of a subject where too much L-glutamate is present, however, leading to excessive levels of glutathione, it may be desirable to decrease or prevent expression of m 5-OPase. Thus, such cells are a particularly suitable host in which to decrease m 5-OPase expression (such as by use of antisense molecules or ribozymes, or through the use of substances which block the expression and/or action of m 5-OPase).

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, DNA encoding the m 5-OPase can be injected into the nucleus of a host cell or transformed into the host cell using a suitable vector, or mRNA encoding the m 5-OPase can be injected directly into the host cell, in order to obtain expression of m 5-OPase in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the m 5-OPase has been introduced can be used to produce (i.e. to functionally express) the m 5-OPase. The function of the encoded mammalian 5-oxoprolinase can be assayed according to methods known in the art (see Meister et al. 1985; Williamson and Meister 1982).

Having identified the nucleic acid molecules encoding m 5-OPase and methods for expressing the m 5-OPase encoded thereby, the invention further provides a method of screening a substance for the ability of the substance to modify 5-oxoprolinase function. The method comprises introducing a nucleic acid molecule encoding the m 5-OPase into a host cell, and expressing the 5-OPase encoded by the molecule in the host cell. The cell is then exposed to a substance and evaluated to determine if the substance modifies the function of the 5-OPase (this modification can be by inhibition of expression of 5-OPase or by blocking the activity of the expressed enzyme). From this evaluation, substances effective in altering the function of the 5-OPase can be found. Such agents may be, for example, 5,5'-dithiobis(2-nitrobenzoic acid) and N-ethylmaleimide (Williamson and Meister 1982).

The evaluation of the cell to determine if the substance modifies the function of the 5-OPase can be by any means known in the art. The evaluation can comprise the direct monitoring of expression of 5-oxoprolinase in the host cell (such as by the method disclosed herein), or the evaluation can be indirect and comprise the monitoring of cleavage of 5-oxoproline to L-glutamate by the 5-oxoprolinase (such as by the method disclosed by Meister et al. 1985 or Williamson and Meister 1982).

The nucleic acid molecules of the subject invention can be used either as probes or for the design of primers to obtain DNA encoding other m 5-OPases by either cloning and colony/plaque hybridization or amplification, such as by using the polymerase chain reaction (PCR) or the ligase chain reaction (LCR) or a combination of both.

Specific probes derived from SEQ ID NO:5 can be employed to identify colonies or plaques containing cloned DNA encoding a member of the m 5-OPase family using known methods (see Sambrook et al. 1989). One skilled in the art will recognize that by employing such probes under suitably high stringency conditions (for example, hybridization at 42° C. with 5×SSPE and 50% formamide, washing at 50–65° C. with 0.5×SSPE), sequences having regions which are greater than 90% homologous or identical to the probe can be obtained. Sequences with lower percent homology or identity to the probe, which also encode m 5-OPases, can be obtained by lowering the stringency of hybridization and washing (e.g., by reducing the hybridization and wash temperatures or reducing the amount of formamide employed).

More particularly, in one embodiment, the method comprises selection of a DNA molecule encoding a m 5-OPase, or a fragment thereof, the DNA molecule having a nucleotide sequence as shown in SEQ ID NO:5, and designing an oligonucleotide probe for m 5-OPase based on SEQ ID NO:5. A genomic or cDNA library of an organism is then probed with the oligonucleotide probe, and clones are obtained from the library that are recognized by the oligonucleotide probe so as to obtain DNA encoding another m 5-OPase.

Specific primers derived from SEQ ID NO:5 can be used in PCR to amplify a DNA sequence encoding a member of the m 5-OPase family using known methods (see Innis et al. 1990). One skilled in the art will recognize that by employing such primers under suitably high stringency conditions (for example, annealing at 50–60° C., depending on the length and specific nucleotide content of the primers employed), sequences having regions greater than 75% homologous or identical to the primers will be amplified.

More particularly, in a further embodiment the method comprises selection of a DNA molecule encoding m 5-OPase, or a fragment thereof, the DNA molecule having a nucleotide sequence as shown in SEQ ID NO:5, designing degenerate oligonucleotide primers based on regions of SEQ ID NO:5, and employing such primers in the polymerase chain reaction using as a template a DNA sample to be screened for the presence of m 5-OPase-encoding sequences. The resulting PCR products can be isolated and sequenced to identify DNA fragments that encode polypeptide sequences corresponding to the targeted region of m 5-OPase.

DNA encoding a m 5-OPase can also be obtained using other methodologies, such as the ligase chain reaction which also utilizes probes and primers devised from SEQ ID NO:5.

Various modifications of the nucleic acid and amino acid sequences disclosed herein are covered by the subject invention. These varied sequences still encode a functional m 5-OPase. The invention thus further provides an isolated nucleic acid molecule encoding a mammalian 5-oxoprolinase, the nucleic acid molecule encoding a first amino acid sequence having at least 90% amino acid identity to a second amino acid sequence, the second amino acid sequence having a sequence as shown in SEQ ID NO:6 and retaining the function of 5-oxoprolinase.

The invention further provides an isolated DNA oligomer capable of hybridizing to the nucleic acid molecule encoding m 5-OPase according to the subject invention. Such oligomers can be used as probes in a method of detecting the presence of m 5-OPase in a sample. More particularly, a sample can be contacted with the DNA oligomer and the DNA oligomer will hybridize to any m 5-OPase present in the sample, forming a complex therewith. The complex can then be detected, thereby detecting presence of m 5-OPase in the sample.

The complex can be detected using methods known in the art. Preferably, the DNA oligomer is labeled with a detectable marker so that detection of the marker after the DNA oligomer hybridizes to any m 5-OPase in the sample (wherein non-hybridized DNA oligomer has been washed away) is detection of the complex. Detection of the complex indicates the presence of m 5-OPase in the sample. As will be readily apparent to those skilled in the art, such a method could also be used quantitatively to assess the amount of m 5-OPase in a sample. Such a quantitative method could be especially useful in samples of tissue or serum of patients having 5-oxoprolinuria, where the amount of m 5-OPase present in the tissue or serum is indicative of the amount of 5-oxoproline that can be converted to L-glutamate.

For detection, the oligomers can be labeled with, for example, a radioactive isotope, biotin, an element opaque to X-rays, or a paramagnetic ion. Radioactive isotopes are commonly used and are well known to those skilled in the art. Representative examples include indium-111, technetium-99m, and iodine-123. Biotin is a standard label which would allow detection of the biotin labeled oligomer with avidin. Paramagnetic ions are also commonly used and include, for example, chelated metal ions of chromium (III), manganese (II), and iron (III). When using such labels, the labeled DNA oligomer can be imaged using methods known to those skilled in the art. Such imaging methods include, but are not limited to, X-ray, CAT scan, PET scan, NMRI, and fluoroscopy. Other suitable labels include enzymatic labels (horseradish peroxidase, alkaline phosphatase, etc.) and fluorescent labels (such as FITC or rhodamine, etc.).

The invention further provides an antibody or fragment thereof specific for the mammalian 5-oxoprolinase encoded by the nucleic acid molecules of the subject invention. Antibodies of the subject invention include polyclonal antibodies and monoclonal antibodies capable of binding to the m 5-OPase, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the $F(ab)_2$, and the Fd fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic m 5-OPase (or an antigenic fragment thereof). Methods for immunization are well known in the art. Such methods include subcutaneous or intraperitoneal injection of the enzyme. One skilled in the art will recognize that the amount of the enzyme used for immunization will vary based on the animal which is immunized, the antigenicity of the enzyme, and the site of injection.

The enzyme which is used as an immunogen may be modified or administered in an adjuvant in order to increase the enzyme's antigenicity. Methods of increasing the antigenicity of an enzyme (i.e., a protein) are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA (enzyme-linked immunosorbent assay), western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art, for example see Sternberger et al. 1970, Bayer et al. 1979, Engval et al. 1972, and Goding 1976.

The labeled antibodies or fragments thereof of the present invention can be used for in vitro, in vivo, and in situ assays to identify cells or tissues which express m 5-OPase, to identify samples containing m 5-OPase, or to detect the presence of m 5-OPase in a sample. More particularly, the antibodies or fragments thereof can thus be used to detect the presence of m 5-OPase in a sample, by contacting the sample with the antibody or fragment thereof. The antibody or fragment thereof binds to any m 5-OPase present in the sample, forming a complex therewith. The complex can then be detected, thereby detecting the presence of m 5-OPase in the sample. As will be readily apparent to those skilled in the art, such a method could also be used quantitatively to assess the amount of m 5-OPase in a sample. Such a quantitative method could be especially useful in samples of tissue or serum of patients having 5-oxoprolinuria, where the amount of m 5-OPase present in the tissue or serum is indicative of the amount of 5-oxoproline that can be converted to L-glutamate.

Fragments of the nucleic acid molecules encoding m 5-OPase are also provided, and are best defined in the context of amino acid sequence relationships among members of the m 5-OPase sequence family as identified according to the subject invention, and in the context of information on the function of specific m 5-OPase domains. Antibodies prepared to the polypeptide encoded by a fragment conserved among m 5-OPase family members would be expected to be of use as reagents capable of detecting many members of the m 5-OPase family. Such antibodies, if introduced into cells that express m 5-OPase, would also be expected to modify the normal function of the m 5-OPases expressed in those cells. In contrast, an amino acid sequence that is less well conserved between the m 5-OPases can be identified in accordance with the subject invention. Antibodies prepared to the polypeptide encoded by this less well conserved fragment would therefore be expected to recognize selectively the m 5-OPase from which the fragment was derived.

Since m 5-OPase is involved in the cleavage of 5-oxoproline to form L-glutamate, which is involved in the formation of glutathione, there are numerous uses of the subject invention. These include the treatment of 5-oxoprolinuria by increasing m 5-OPase production, or the treatment of glutathione deficiencies by increasing m 5-OPase production (thereby increasing production of L-glutamate which is then involved in glutathione production).

As indicated above, levels of m 5-OPase in a cell can be increased by introducing the nucleic acid molecule encoding m 5-OPase into the cell and by expressing the m 5-OPase encoded thereby. For in vivo expression of m 5-OPase, various gene therapy techniques can be utilized to get the nucleic acid molecule into the desired cell. As should be readily apparent, the nucleic acid molecule encoding m 5-OPase needs to be targeted to the desired cells by known methods, since in other cells of the patient decreased expression of m 5-OPase may simultaneously or also be desirable.

As also indicated above, levels of m 5-OPase in a cell can be decreased by introducing an antisense or ribozyme construct into the cell. An antisense construct blocks translation of mRNA encoding m 5-OPase into the m 5-OPase enzyme. A ribozyme construct cleaves the mRNA encoding the m 5-OPase thus also preventing expression of functional m 5-OPase enzyme. For in vivo decreasing of expression of m 5-OPase, various gene therapy techniques can again be utilized to introduce the antisense or ribozyme construct into the desired cell. The construct needs to be targeted to the desired cells by known methods, since in other cells of the patient increased expression of m 5-OPase may simultaneously or also be desired.

It should be readily apparent to those skilled in the art that it may be desirable for the m 5-OPase molecule of the subject invention to include a leader sequence for targeting of the m 5-OPase protein to a desired part of a cell. Such leader sequences are well known in the art. It should also be readily apparent to those skilled in the art that the met residue at the amino terminal of the amino acid sequence shown in SEQ ID NO:6 may not need to be present in the mature m 5-OPase enzyme (or the ATG at the 5' end of the nucleotide sequence of SEQ ID NO:5), and are provided in order to express the enzyme in a host cell. The met or non-met versions of m 5-OPase are thus specifically intended to be covered by reference to SEQ ID NO:5 or SEQ ID NO:6. It may be desirable when expressing the m 5-OPase in a host cell to introduce a nucleotide sequence which includes a leader sequence and the m 5-OPase encoding sequence (such as SEQ ID NO:5). After expression of the leader/m 5-OPase fusion protein, the leader targets the m 5-OPase protein within the cell before the leader peptide is cleaved from the mature m 5-OPase protein.

SEQ ID NO:7 represents the entire open reading frame (ORF) of the rat m 5-OPase (SEQ ID NO:5), as well as the 5' and 3' untranslated regions. More particularly, nucleotides 1–105 of SEQ ID NO:7 are the 5' untranslated portion, and nucleotides 106–108 of SEQ ID NO:7 are the start codon. Nucleotides 109–3969 of SEQ ID NO:7 encode the mature rat m 5-OPase enzyme, and nucleotides 3970–3972 represent the TGA stop codon. The remaining nucleotides of SEQ ID NO:7 represent the 3' untranslated region.

5-Oxoprolinase(5-OPase, E.C.3.5.2) catalyzes a reaction in which the endergonic cleavage of 5-oxo-L-proline to form L-glutamate is coupled to the exergonic hydrolysis of ATP to ADP and inorganic phosphate. Highly purified preparations of the enzyme have been obtained from rat kidney and *Pseudomonas putida*. The rat kidney enzyme is composed of two strongly interacting, apparently identical subunits ($M_r$:142,000), whereas that from *Pseudomonas putida* is composed of two functionally different protein components that can readily be dissociated. The subject invention provides the cloning of rat kidney 5-oxoprolinase, together with preliminary expression studies. cDNA clones encoding the enzyme were isolated by screening a λgt11 cDNA library beginning with a degenerate oligonucleotide probe based on peptide sequence data obtained from the purified enzyme. The whole cDNA clone was completed by amplifying its 5'-end from a premade library of rat kidney Marathon-Ready™ cDNAs using PCR methodology. The composite cDNA (4,016 bases, SEQ ID NO:7) revealed an uninterrupted open reading frame encoding 1,288 amino acid residues (SEQ ID NO:6) ($M_r$:137,759). The deduced amino acid sequence contains all four of the peptide sequences that were independently found in peptide fragments derived from the enzyme. Expression of the full length clone in *E. coli* yielded a product of the same size as the rat kidney enzyme and the product reacted with antibodies directed against the rat kidney enzyme. The predicted amino acid sequence is almost 50% identical, throughout its entire length, to that of a hypothetical yeast protein YKL215C. It is also homologous in half its length to the bacterial hydantoinase HyuA, and in the other half to the bacterial hydantoinase HyuB. The results suggest unexpected evolutionary relationships among the hydantoinases and rat kidney 5-oxoprolinase, which share the common property of hydrolyzing the imide bond of 5-membered rings, but which do not all require ATP.

MATERIALS AND METHODS

Materials: Frozen rat kidneys were obtained from Pel-Freez. Ultrogel AcA34 was from LKB. Phenyl-and Aminohexyl-Sepharose were obtained from Pharmacia. DEAE-Cellulose(DE-52) was from Whatman. The rat kidney λgt11 cDNA library, premade Rat Kidney Marathon-Ready™ cDNAs and Taq-start antibody were purchased from Clontech. DNA polymerase for PCR amplification (long-distance polymerase chain reaction or LD-PCR system) was from Boehringer-Mannheim. Restriction endonucleases were from New England Biolabs. All radioisotopes were obtained from Amersham. All chemicals and biologicals were purchased from Sigma unless noted otherwise.

General Methods: Standard molecular biology techniques were used (Sambrook et al. 1989). Recombinant lambda DNA purification was performed as described (Ausubel et al. 1988). cDNA clones were subcloned into a Bluescript II KS vector (Stratagene) and sequenced by the dideoxy chain termination method (Sanger et al. 1977) with Sequenase (United States Biochemical) using T3, T7 primers or specific internal primers. Automated DNA sequencing was carried out at the Cornell University DNA Synthesis and Sequencing Facility.

Determination of Enzyme Activity: Enzyme activity was determined (Williamson and Meister 1982) in reaction mixtures containing (final volume, 0.5 ml), 100 mM Sodium Hepes buffer (pH8.0), 2 mM 5-oxo-L-proline (containing 100 cpm/nmol of 5-oxo-L-[U-$^{14}$C]proline), 5 mM ATP, 8 mM $MgCl_2$, 2 mM PEP, 150 mM KCl, 2 mM DTT, pyruvate kinase (5 units), and 5-OPase. After incubation at 37° C. for 30 min, the reaction mixtures were treated with 0.1 volume of 1 M HCl and placed at 0° C. for 5 min; an equal volume of 1 M Tris was then added. Denatured proteins were removed by centrifugation. Portions of the neutralized reaction mixtures were then analyzed for [$^{14}$C]-glutamate by liquid scintillation counting after removal of unreacted 5-oxoproline by chromatography on Dowex 50 ($H^+$) as described (Williamson and Meister 1982). One unit of activity is defined as the amount of enzyme needed for the production of 1.0 μmol of glutamate per hour under standard assay conditions.

Purification of 5-OPase: Rat kidney 5-OPase was isolated from rat kidney homogenates using a procedure developed by Williamson and Meister (1982). The homogenate was first centrifuged (16,200×g, 90 min) and the proteins in the supernatant solution were fractionated by ammonium sulfate precipitation. The fraction containing the enzyme activity was then processed by a series of column chromatography steps, which sequentially involved DEAE-cellulose (DE-52), Ultrogel AcA34, Phenyl-Sepharose, AH-Sepharose and a second Ultrogel AcA34 step, as described (Williamson and Meister 1982). The preparation of the enzyme was further processed by a second DE-52 step and a third Ultrogel AcA34 chromatography step. An almost homogeneous (>90% pure) preparation of the enzyme with a specific activity of 72 units/mg was obtained in about 20% yield. Every step of the purification was followed by SDS-PAGE analysis. Quantitative assay for protein was done by the method of Bradford (1976).

Preparation of Antibody Against Rat Kidney 5-OPase: The 5-OPase (300 μg) was dialyzed for 24 hrs against two changes of phosphate-buffered saline (PBS) and was concentrated to a final volume of 600 μl by vacuum dialysis against PBS. An equal volume of complete Freund's adjuvant was added to the enzyme and mixed vigorously until the solution became very viscous. Two anesthetized New Zealand white rabbits (~1.8 kg) were injected intradermally at 20 sites (20–25 μl of emulsion each). A test bleed was performed two weeks after the primary immunization. The titer and specificity of the antibodies were determined by ELISA and Western blot analysis, respectively.

Amino Acid Sequences of Peptides from 5-OPase: Approximately 5 μg (1.5 pmol) of the protein isolated from rat kidney was electrophoresed on a 7.5% SDS-polyacrylamide gel and electrotransferred to a PVDF (poly (vinylidene difluoride)) membrane (Matsudaira 1987). The membrane was stained with Amido black and the protein band corresponding to 5-OPase (~140 kDa) was cut out for solid-phase enzymatic digestion (endopeptidase Lys-C, enzyme/substrate: 1/10) (Fernandez 1992). The microbore HPLC-purification and sequencing of the peptides were carried out at the Rockefeller University Protein & Peptide Sequencing Facility.

cDNA Cloning of Rat Kidney 5-OPase: A 29 mer degenerate oligonucleotide, oligonucleotide 1, SEQ ID NO:8:

(GTITTC(T)CAA(G)GAA(G)GAA(G)GCIGTIACIGAA (G)GC) was synthesized based on the peptide sequence VFQEEAVTEA (SEQ ID NO:9) in peptide 2 (SEQ ID NO:2) (see Table I), end-labeled with [γ-$^{32}$P]ATP, and used to screen a λgt11 rat kidney cDNA library. The probe is a mixture of 32 different 29 mer oligonucleotides corresponding to all codon combinations derived from peptide 2. Deoxyinosine (I) was substituted at the wobble positions in four of the codons. Duplicate filters were prehybridized at 42° C. for 3 hrs in prehybridization solution (6×SSC, 5×Denhardt's solution, 0.5% SDS, 0.01% sodium pyrophosphate and 100 μg/ml denatured, fragmented salmon sperm DNA), followed by hybridization at 50° C. for 18 hrs in the same solution containing 1.6×10$^5$ cpm of $^{32}$P-labeled probe per ml of hybridization buffer. The filters were washed with 2×SSC containing 0.5% SDS for 20 min at room temperature with one change of the wash buffer, followed by washing with 2×SSC, 0.2% SDS at 50° C. for 40 min with one change of the buffer. Of the ~5×10$^5$ clones that were screened, three positives were identified, plaque-purified and subcloned into Bluescript II KS (Stratagene). These three clones, designated as CL33, 91 and 99, contained inserts of 1.3, 1.5 and 0.8 kb, respectively; CL91 also contained a poly(A) tail. CL33 and CL91 were sequenced completely. The position of these clones in the ultimately derived sequence, and that of the relevant clones described below, are shown in FIG. 1.

A 0.39 kb PstI/EcoRI fragment was prepared from the 5'-end of CL33 and labeled with [α-$^{32}$P]dCTP by nick-translation (1×10$^8$ cpm/μg) for use as a probe for the second screening of the same library. Duplicate filters were hybridized at 55° C. in 6×SSC hybridization solution (same as above) with 1.0×10$^5$ cpm of $^{23}$P-labeled probe per ml hybridization solution. After rinsing briefly in 2×SSC/0.5% SDS at room temperature, the filters were washed in 0.4× SSC/0.1% SDS for 40 min at 55° C. with one change of the wash buffer. Of the ~5×10$^5$ clones that were screened, 32 positives were identified, plaque-purified and DNA prepared. Their insert sizes ranged from 1.1 to 3.2 kb. Southern blot analysis revealed that 14 of them hybridized with an oligonucleotide probe (17 mer) which is close to the 3'-end of CL33 and CL91. This result indicated that these 14 clones overlapped completely with CL33 and CL91. One of these 14 clones, CL241, was chosen for subcloning and 5' and 3'-end sequencing analysis because it represented a relatively large insert (~2.0 kb). Another four clones (all contain inserts >2.0 kb), CL222, 252, 273, and CL282, were chosen from the 18 clones which did not hybridize with the oligonucleotide probe. CL273 and CL282, the two apparently most 5'-extended clones, as well as CL241, were subjected to restriction mapping and complete sequencing. CL273 proved to be an artifact, as described further below.

A 0.8 kb EcoRV/XbaI fragment was prepared from the 5'-end of CL282 and used as a probe for further screening of the library. Fourteen positive clones were obtained. In order to quickly screen the most 5'-extended clones, a 24 mer primer (antisense primer), complementary to nt 100–123 of CL282 (nt 744–764 in SEQ ID NO:7), was synthesized and used to amplify the 5'-extended region of the 14 positive clones with PCR according to the manufacturer's instructions. The sense primer used here was one of the two primers of the λgt11 cDNA insert Amplifier (Clontech). Three positive clones, CL341, CL342 and CL361, seemed to contain relatively longer sequences in the 5'-end region and were subjected to subcloning, restriction mapping, and sequencing, although CL341 proved to be another artifact (see below).

In order to obtain a complete cDNA clone, three antisense gene specific primers (GSP1, GSP2 and GSP3, which are complementary to nt 254–277, 744–764, and 1414–1434 in SEQ ID NO:7, respectively) were designed and used to amplify the 5'-cDNA end of 5-OPase from a premade rat kidney Marathon-Ready™ cDNAs (Clontech) with the provided adaptor specific primer, AP1 (Chenchik et al. 1995). PCR (30 cycles) was performed according to the manufacturer's instruction with the LD-PCR System (Boehringer-Mannheim) in a Perkin-Elmer DNA Thermal Cycler 480 using the following program: 94° C. for 1.0 min, then 30 cycles of 94° C. for 30 sec., 63° C. for 45 sec and 68° C. for 1.5 min. 5 μl of the PCR products were subjected to electrophoretic examination on a 1.2% agarose/EtBr gel. A secondary PCR reaction was performed following the same procedure described above except that 5 μl of the diluted (1:10) primary PCR product was used in place of the Marathon-Ready cDNAs as template, and 25 cycles were applied. After the secondary PCR amplification, the products were gel-purified, digested with ApaI/NotI (for CGSP2) or HincII/NotI (for CGSP3), subcloned into Bluescript II KS which had been previously digested with ApaI/NotI or HincII/NotI, and sequenced.

Northern Plot Analysis: A charged nylon membrane containing mRNA from various rat tissues (Clontech) was used. The membrane was incubated in prehybridization buffer (5×SSPE containing 10×Denhardt's solution, 50% formamide, 2% SDS, and 100 μg/ml denatured, fragmented salmon sperm DNA) at 42° C. with CL33, which was labeled with $^{32}$P by nick-translation (5×10$^8$ cpm/mg). The membrane was washed twice for 10 min each with 2×SSPE/ 0.05% SDS at room temperature and twice for 40 min at 50° C. in 0.1×SSPE/0.1% SDS. Autoradiography was performed at −79° C. for 3 days.

Construction of Expression Plasmids for 5-OPase (full-length and terminal deleted mutants): An N-terminal truncated cDNA clone of 5-OPase was constructed by joining the overlapped clones of CL361, CL282 and CL241 using the unique restriction sites of HincII and AgeI (FIG. 1). The assembled 3.8 kb cDNA clone, which contains a stop codon at its 3'-end, was excised from the recombinant Bluescript II KS by EcoRI digestion and ligated to pT7-7(19) which had been digested with EcoRI. The resulting clone, pFCL361-241, which is truncated at the N-terminal of 5-OPase by 54 residues, is in the proper reading frame in the EcoRI site of pT7-7 and would subsequently be translated as a fusion protein linked through its amino terminus to the first 4 amino acids of the gene 10 protein.

Another N-terminal deleted clone (truncated by 850 residues at the N-terminal of 5-OPase), pFCL33, was constructed directly by joining the cDNA insert of CL33 into pT7-7 at the EcoRI site. The resulting clone, pFCL33, would also subsequently be translated as a fusion protein linked through its amino terminus to the first 4 amino acids of the gene 10 protein.

Creation of the NdeI site at the start codon of 5-OPase was achieved by PCR amplification from rat kidney Marathon-Ready cDNAs using SEQ ID NO:10: 5'-CTCCAGCTTCAACCATATGGGCAGC-3' as the gene specific primer. The LD-PCR amplification resulted in a full-length cDNA clone of 5-OPase (4.0 kb). This clone was digested with NdeI/PstI, yielding a 2.9 kb cDNA fragment that was truncated at the C-terminal region of 5-OPase by 302 amino acid residues, and was ligated to pT7-7 which had previously been digested with NdeI/PstI. For subsequent expression as a fusion protein, the resulting clone (pFCPCR) was linked at its 3' end to the DNA sequence encoding the hexapeptide AQAYHR followed by a stop codon.

The full-length clone was constructed by ligation of the NdeI/KpnI fragment of pFCPCR to pFCL361-241 which had been digested with NdeI/KpnI. The constructed full-length clone, PROPASE (deposited with the ATCC under Accession No. 98272), is immediately downstream from the T7 promoter (φ10). Sequences representing the full length and truncated recombinant 5-OPase were expressed in *E. coli* (BL21:DE3) as described (Studier et al. 1990).

EXAMPLE I

Isolation of 5-OPase from Rat Kidney and Its Peptide Sequences: The enzyme preparation obtained from step 9 of the purification procedure yields, as monitored by SDS-polyacrylamide gel electrophoresis, a dominant band of 140 kDA that comprises >90% of the protein and two minor bands of lower molecular weight. Approximately 600 μg of protein could be obtained from 500 g of frozen rat kidney with a specific activity of 72 units/mg. Table I shows the sequences of four Lys-C enzymatic peptides obtained from the purified enzyme. The amino acid sequences corresponding to these four peptides were subsequently found in the cDNA clone.

EXAMPLE II

Isolation of cDNA clones coding for 5-OPase: FIG. 1 outlines the position in the cDNA sequence of the relevant clones used for sequence determination. Letters indicate restriction sites for EcoRI (E), XbaI (X), KpnI (K), ApaI (A), HincII (H), AgeI (G), and PstI (P). By screening a rat kidney cDNA library with the end-labeled, degenerate oligonucleotide probe encoding the partial sequence of peptide 1, three positive clones were initially obtained. Two of them, CL33 and CL91 were found to contain the longest sequence of the 3'-untranslated region. CL91 also included a poly(A) tail. Screening of the same library, using the 0.39 Kb $^{32}$P-labeled EcoRI/PstI fragment prepared from the 5'-end of CL33, gave 32 positives. Of these, CL241, 222 and 282 were completely sequenced. Though CL273 was the largest (3.2 kb) and the most 5'-extended, this clone was found to be an artifact at its 5'-region on the basis of restriction mapping and sequencing; i.e., about 2/3 of the 5' terminal region of CL273 was from an unknown cDNA clone, as judged in part by the presence of a poly(A) tail in this region. CL341, the most 5'-extended cDNA clone (2.4 kb) from the third screening (which used a probe from the 5' end of CL282) was also found to be incorrect; restriction mapping and sequencing of this clone indicated that a fragment of 0.6 kb at its 5'-end was an artifact, as evidenced by the presence of a number of internal stop codons. CL324 and 361 from the third screening allowed determination of most of the remaining sequence.

The complete cDNA clone for the enzyme was obtained by LD-PCR amplification using the premade rat kidney Marathon-Ready cDNAs as templates. After secondary PCR amplification as described under the "Experimental Procedures", the resulting PCR product generated a band of the predicted size after electrophoresis on a 1.2% agarose/EtBr gel. Sequencing of the clones of CGSP2 and CGSP3 revealed two completely overlapping cDNA fragments of the 5'-end of 5-oxoprolinase, in which CGSP3 was more 51-extended than CGSP2 by 4 bases.

The sequence of the assembled 4.016 kb cDNA for rat kidney 5-OPase is shown in SEQ ID NO:7. It revealed an uninterrupted open reading frame (SEQ ID NO:5) encoding 1,288 amino acid residues (SEQ ID NO:6) with a calculated molecular weight of 137,759, which agrees well with that previously estimated by SDS/PAGE ($M_r$:142,000) (Williamson and Meister 1982). The 5'-untranslated region of 105 nucleotides contains an in-frame stop codon. The first ATG (position 106 of SEQ ID NO:7) is presumed to be the initiation codon and conforms to the consensus sequence for an initiation codon context (Kozak 1984). The coding sequence ends with a termination codon (TGA) at position 3,969 of SEQ ID NO:7, followed very closely by the polyadenylation signal AATAAA beginning at position 3981 of SEQ ID NO:7 and a 14 nucleotide poly(A) tail.

EXAMPLE III

Analysis of The Predicted Amino Acid Sequence of Rat Kidney 5-OPase: All four independently determined peptide sequences are found in the deduced amino acid sequence (SEQ ID NO:6). The sequence also indicates five potential sites for N-glycosylation (N-X-S/T) (residues 697, 698, 919, 1003 and 1106 of SEQ ID NO:6), although actual glycosylation has not been demonstrated. The calculated amino acid composition is in fair agreement with the amino acid analysis of the isolated protein (Williamson and Meister 1982), except for Asx, Glx and Lys. The predicted protein sequence was found to be unique when compared with the protein sequences given in the GenBank and SwissProt data bases, but strong homologies with three other proteins were found (see below).

EXAMPLE IV

Tissue mRNA Expression: Northern blot hybridization studies with nick-translated probe prepared from a fragment of 5-OPase (CL33) showed that the mRNA for the enzyme is well expressed in testis, kidney and liver, whereas the mRNA levels in other tissues examined (brain, heart, lung, spleen and muscle) were about 10' or less of that found in testis or kidney. These findings are in general agreement with determinations of the activities of 5-OPase in these tissues (Van Der Werf et al. 1975). The size of the transcript in kidney (~4.4 kb) is a little smaller than that found in testis and liver (~5.0 kb). Minor bands of smaller size, particularly evident in the testis sample, probably arise from mRNA degradation or from non-specific hybridization. It should be noted that the Rat Multiple Tissue Northern Blot (Clontech) used in this study had been probed several times before, so the strength of the hybridization signal does not represent the real level of the mRNA.

EXAMPLE V

Expression of Recombinant 5-OPase: The expressed recombinant rat kidney 5-OPase and the expressed N-terminal and C-terminal truncated proteins gave bands of the predicted sizes when analyzed by SDS-gel electrophoresis and Western blot using the antibodies against the purified 5-OPase. Also, recombinant 5-OPase and the 5-OPase isolated from rat kidney homogenate gave bands of apparently same size when detected by Western blot. These data provide further evidence that the cDNA clone obtained in this study corresponds to that of rat kidney 5-OPase. The C-terminal truncated recombinant 5-OPase (missing a C-terminal peptide of 243 residues), encoded by pFCPCR, gave no detectable band on the Western blot, but its expression was readily seen when gels were stained with Coomassie. This result suggests that the polyclonal sera principally contain antibodies that recognize denaturation-resistant epitopes within the C-terminal region of 5-OPase. Enzymatic activity analysis of the expressed recombinant rat kidney 5-OPase in the lysate of *E. coli*, using standard procedures (see Materials and Methods), indicated no significant increase in activity above the control.

EXAMPLE VI

The subject invention provides for the cloning and expression of 5-oxoprolinase. The deduced amino acid sequence of the rat kidney enzyme consists of 1,288 residues (SEQ ID NO:6) with a calculated molecular weight of 137,759, which is close to the weight of 142,000 previously estimated from SDS-PAGE analysis of the isolated enzyme (Williamson and Meister 1982). Previous work (Van Der Werf and Meister 1974; Williamson and Meister 1982) in this laboratory also suggested that the native enzyme ($M_r$:325,000, estimated by gel filtration) is composed of 2 subunits of identical molecular weight that are not held together by disulfide bonds. Since all of the four independently determined peptide sequences were found within the predicted protein sequence and the calculated amino acid composition was in fair agreement with the amino acid analysis of the isolated rat kidney enzyme, the data support the suggestion that the two subunits are identical.

Most of the cDNA sequence of 5-OPase presented here represents the overlapping cDNA clones that were obtained from successive screening of a λgt11 rat kidney cDNA library. However, further screening of the same library with probes directed to the 5'-terminal region failed to produce positive results. Accordingly, to determine the 5'-terminal sequence of the enzyme, the rat kidney Marathon-Ready cDNAs were turned to. Marathon-Ready cDNAs are pre-made libraries of adaptor-ligated double strand cDNA ready for use as templates in Marathon cDNA amplification, a unified method for performing rapid amplification of both 5'- and 3'-cDNA ends (RACE) from the same template (Chenchik et al. 1995) with the LD-PCR method (Barnes 1994). In the present studies, the cDNA of rat kidney 5-OPase was completed by amplifying its 5'-end from a library of rat kidney Marathon-Ready cDNAs. Three primers, which were complementary to the known sequences at various regions of the cDNA, were designed and used as gene-specific primers to perform the 5'-RACE. They each gave the product of the predicted size. Sequencing of CGSP2 and CGSP3 revealed that they were completely overlapped except for a several base extension at the 5'-end of CGSP3. Sequencing of the 5'-end of another 5'-RACE product gave the same results as CGSP3.

The full-length (beginning just before the start codon) and the 3' end cDNA of 5-OPase have also been amplified from Marathon-ready cDNAs and their sequences confirmed by restriction mapping and DNA sequencing, giving the same results as obtained from the conventional screening of the λgt11 cDNA library. This indicates that the library of rat kidney Marathon-Ready cDNAs contains the full-length cDNA of 5-OPase and that the cDNA clones from conventional screening of the λgt11 cDNA library are consistent with those obtained from Marathon-Ready cDNAs by LD-PCR amplification. Thus, the cDNA clone of rat kidney 5-OPase obtained in this study has been checked by two different methods.

Western blot and standard SDS-PAGE analysis of the proteins encoded by the recombinant 5-OPase clones demonstrated that the full length recombinant 5-OPase expressed in E. coli migrates at a position identical to that of endogenous rat kidney 5-OPase, further demonstrating that the isolated cDNA corresponds to that encoding the rat kidney enzyme. Similar analysis of proteins encoded by the truncated recombinant cDNA clones revealed that recombinant proteins with intact C-terminal regions are specifically detected by the antiserum against the isolated rat kidney 5-OPase, whereas the C-terminal truncated recombinant proteins were not detected by the antiserum. The results indicate that the C-terminal 243 residues of 5-OPase contain the reactive denaturation-resistant epitopes for the anti-5-OPase serum, and that other regions of the enzyme either do not contain such epitopes or that their epitopes are unreactive in the absence of the C-terminal region.

The unexpected result from this study is the demonstration of homology between rat kidney 5-OPase, the two bacterial hydantoinases and the yeast protein YKL215C. YKL215C is a hypothetical protein of 1,287 residues encoded by the URA1-RSD1 integenic region (Tzermia et al. 1994). The homology of this sequence and that of the rat kidney enzyme is sufficiently strong (48.4% identity) as to suggest that the yeast protein is also a 5-oxoprolinase. To understand the homology with the bacterial hydantoinases, a comparison of the 5-oxoprolinase reaction and that catalyzed by the hydantoinases indicates the similarity of the chemical reactions involved. Both reactions involve the hydrolysis of 5-membered rings via hydrolysis of their internal —CO—NH— bonds. HyuA is specific for D-5-substituted hydantoins, while HyuB is specific for the corresponding L isomers (Watabe et al. 1992; LaPointe et al. 1994). The amino-terminal half of rat kidney 5-oxoprolinase shows 26.6% identity with the amino-terminal region of HyuA, while the carboxyl-terminal half of the rat kidney enzyme shows 25.9% identity with the amino-terminal region of HyuB. These somewhat surprising relationships partially reflect the fact that HyuA and HyuB show no significant homology to each other (Watabe et al. 1992; LaPointe et al. 1994). Thus it is possible that the rat kidney enzyme evolved from an evolutionary fusion of these functionally similar, but structurally different, enzymes—or that the hydantoinases arose from an enzyme related to rat kidney 5-oxoprolinase. However, it is relevant that neither HyuA or HyuB require ATP for ring hydrolysis, in contrast not only to 5-OPase, but also to a different bacterial hydantoinase that cleaves 5-substituted hydantoins (Yamashiro et al. 1988) as well as to one that cleaves N-methylhydantoins (Kim et al. 1987). The difference among the bacterial hydantoinases in their requirement for ATP is surprising, and it will clearly be of interest to learn the structural relationship of rat kidney 5-OPase to the ATP-requiring hydantoinases.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE I

Sequences of peptides derived from purified rat kidney 5-OPase and comparison with the sequence of the protein deduced from its cDNA. Sequences are identical except where noted. Underlined residues are those derived from the cDNA sequence that align with residues which were not identified with certainty by peptide sequencing.

| Peptide | Amino acid sequence | Positions in cDNA sequence |
|---|---|---|
| 1 | IQTGPPHVEK (SEQ ID NO: 1) | 652–661 |
| 2 | LVQGGVFQEEAVTEALRAP(G)K (SEQ ID NO: 2)<br>                  G | 886–906 |
| 3 | ??A(C) (S)G(T)N(N) (L)HDN(S)DLRAQVAANQK (SEQ ID NO:3)<br>ISG C   S   T R N   L    S | 907–932 |
| 4 | ??RTVNLGGK (SEQ ID NO: 4)<br>DG | 1223–1232 |

LIST OF REFERENCES CITED

Ausubel, F. M., et al., "Current Protocols in Molecular Biology", Greene Publishing Associates/Wiley-Interscience, New York (1988).

Barnes, W. M., Proc Natl Acad Sci USA 91:2216–2220 (1994).

Bayer, E. A., et al., Meth Enzym 62:308 (1979).

Bordo, D. and Argos, P., J Mol Biol 217:721–729 (1991).

Bradford, M., Anal Chem 72:248–255 (1976).

Campbell, A. M., Monoclonal Antibody Technology: Laboratory Techniques in Biochemistry and Molecular Biology, Elsevier Science Publishers, Amsterdam, The Netherlands (1984).

Capecchi, M., Cell 22:479–488 (1980).

Chenchik, A., et al., CLONTECHniques X(1), 5–8 (1995).

Chrisey, L., et al., Antisense Research and Development 1(1):57–63 (1991).

Christoffersen, R. E. and Marr, J. J., Journal of Medicinal Chemistry 38(12):2023–2037 (1995).

Dolphin, D., et al., "Glutathione: Chemical, Biochemical, and Medical Aspects", Parts A and B, "Coenzyme and Cofactors Series", Vol. III, John Wiley, New York (1989).

Engval, E., et al., Immunol 109:129 (1972).

Fernandez, J., et al., Anal Biochem 201:255–264 (1992).

French, S. and Robson, B., J Molecular Evolution 19:171–175 (1983).

Goding, J. W., J Immunol Meth 13:215 (1976).

Han, L., et al., Proc Natl Acad Sci USA 88:4313–4317 (1991).

Huang, C.-S., et al., J Biol Chem 268:19675–19678 (1993).

Innis, et al., PCR Protocols, Academic Press, San Diego, Calif. (1990).

Kim, J. M., et al., Biochem Biophys Res Commun 142:1006–1012 (1987).

Klein, T. M., et al., Nature 327:70–73 (1987).

Kozak, M., Nucleic Acids Res 12:857–872 (1984).

LaPointe, G., et al., Applied and Environmental Microbiology 60:888–895 (1994).

Li, L., et al., J Biol Chem 263:6495–6501 (1988).

Li, L., et al., J Biol Chem 264:3096–3101 (1989).

Lutz, et al., Exp Cell Res 175:109–124 (1988).

Mannino, R. J. and Gould-Fogerite, S., BioTechniques 6:682–690 (1988).

Matsudaira, P., J Biol Chem 262:10035–10038 (1987).

Mazelis, M., and Creveling, R. K., Plant Physiol 62:798–801 (1978).

Meister, A., in "The Enzymes" (Boyer, P. D., ed) 3rd Ed, Vol. 10, pp. 671–691, Academic Press, N.Y. (1974).

Meister, A., et al., Methods Enzymol 113:445–451 (1985).

Meister, A., and Larsson, A., in "The Metabolic and Molecular Bases of Inherited Disease", Scriver, C. R., et al., eds, 7th Ed., McGraw Hill, N.Y. (1995).

Miller, L. K., Bioessays 11:91–95 (1989).

Mooz, E. D., and Wigglesworth, L., Biochem Biophys Res Commun 68:1066–1072 (1976).

Richman, P., and Meister, A., J Biol Chem 250:1422–1426 (1975).

Rossi, J. J., et al., AIDS Research and Human Retroviruses 8(2):183–189 (1992).

Rossi, J. J., British Medical Bulletin 51(1):217–225 (1995).

Sambrook, J., et al., "Molecular Cloning: A Laboratory Manual", 2nd Ed., Cold Spring Harbor Laboratory, Cold Spring Harbor, NY (1989).

Sanger, F., et al., Proc Natl Acad Sci USA 74:5463–5467 (1977).

Sarver, N., et al., Science 247:1222–1225 (1990).

Seddon, A. P., et al., J Biol Chem 259:8091–8094 (1984).

Seddon, A. P., and Meister, A., J Biol Chem 261:11538–11541 (1986).

Shigekawa, K. and Dower, W. J., BioTechniques 6:742–751 (1988).

Snoke, J. E., and Bloch, K., J Biol Chem 199:407–414 (1952).

Snoke, J. E., J Biol Chem 213:813–842 (1955).

Sternberger, L. A., et al., J Histochem Cytochem 18:315 (1970).

St. Groth, et al., J Immunol Methods 35:1–21 (1980).

Studier, F. W., et al., Methods Enzymol 185:60–89 (1990).

Taylor, W. R., J Theor Biol 119:205–218 (1986).

Tzermia, M., et al., Yeast 10:663–679 (1994).

Van Der Werf, P., et al., Proc Natl Acad Sci USA 68:2982–2985 (1971).

Van Der Werf, P., and Meister, A., Biochem Biophys Res Commun 56:90–96 (1974).

Van Der Werf, P., et al., J Biol Chem 250:6686–6692 (1975).

Watabe, K., et al., J Bacteriol 174:962–969 (1992).

Williamson, J. M., and Meister, A., J Biol Chem 257:9161–9172 (1982).

Yamashiro, A., et al., Agric Biol Chem 52:2857–2863 (1988).

What is claimed is:

1. An isolated nucleic acid molecule encoding a rat 5-oxoprolinase, wherein the isolated nucleic acid molecule has (i) a nucleotide sequence according to SEQ. ID. No. 5, (ii) a nucleotide sequence which hybridizes to the nucleotide sequence according to SEQ. ID. No. 5 under stringency conditions of 5×SSPE and 50 percent formamide at 42° C. and remains hybridized after washing with 0.5×SSPE at 50 to 65° C. or (iii) a nucleotide sequence encoding a protein or polypeptide having an amino acid sequence of SEQ. ID. No. 6.

2. The isolated nucleic acid molecule of claim 1 wherein said nucleic acid is deoxyribonucleic acid.

3. The isolated nucleic acid molecule of claim 2 wherein said deoxyribonucleic acid is cDNA.

4. The isolated nucleic acid molecule of claim 1 wherein said nucleic acid molecule has a nucleotide sequence according to SEQ. ID. No. 5.

5. The isolated nucleic acid molecule of claim 1 wherein said nucleic acid molecule encodes a protein or polypeptide having an amino acid sequence according to SEQ. ID. NO. 6.

6. The isolated nucleic acid molecule of claim 1 wherein said nucleic acid is ribonucleic acid.

7. The isolated nucleic acid molecule of claim 6 wherein said ribonucleic acid is mRNA.

8. A method of decreasing expression of a mammalian 5-oxoprolinase in an in vitro host cell, said method comprising introducing into the host cell a nucleic acid molecule having a nucleotide sequence of at least 20 nucleotides in length which is complementary to the mRNA of claim 7, wherein the nucleic acid molecule blocks translation of complementary mRNA to decrease expression of the mammalian 5-oxoprolinase in the host cell.

9. A method of decreasing expression of a mammalian 5-oxoprolinase in an in vitro host cell, said method comprising:

introducing into the host cell a ribozyme nucleic acid molecule having a recognition sequence complementary to a portion of the mRNA of claim 7, wherein expression of said ribozyme nucleic acid molecule in said host cell results in decreased expression of said mammalian 5-oxoprolinase in said host cell.

10. A cell comprising the nucleic acid molecule of claim 1.

11. An expression vector comprising the nucleic acid molecule of claim 1.

12. The expression vector of claim 11 wherein said expression vector is selected from the group consisting of a plasmid and a virus.

13. A cell comprising the expression vector of claim 11.

14. A method of increasing expression of rat 5-oxoprolinase in an in vitro host cell, said method comprising:
   introducing the nucleic acid molecule of claim 1 into the host cell; and
   allowing said host cell to express said nucleic acid molecule resulting in the production of rat 5-oxoprolinase in said host cell.

15. A method of obtaining DNA encoding a mammalian 5-oxoprolinase, said method comprising:
   selecting a DNA molecule encoding a rat 5-oxoprolinase, said DNA molecule having a nucleotide sequence as shown in SEQ ID NO:5;
   designing an oligonucleotide probe for a 5-oxoprolinase based on SEQ ID NO:5;
   probing a genomic or cDNA library of an organism with the oligonucleotide probe; and
   obtaining clones from said library that are recognized by said oligonucleotide probe, so as to obtain DNA encoding a mammalian 5-oxoprolinase.

16. A method of obtaining DNA encoding a mammalian 5-oxoprolinase, said method comprising:
   selecting a DNA molecule encoding a rat 5-oxoprolinase, said DNA molecule having a nucleotide sequence as shown in SEQ ID NO:5;
   designing degenerate oligonucleotide primers based on SEQ ID NO:5; and
   utilizing said oligonucleotide primers in a polymerase chain reaction on a DNA sample to identify homologous DNA encoding a mammalian 5-oxoprolinase in said sample.

17. A nucleic acid oligomer which hybridizes to the nucleic acid molecule of claim 4 under stringency conditions of about 5×SSPE and about 50 percent formamide at about 42° C. and remains hybridized after washing with about 0.5×SSPE at about 50 to about 65° C.

18. A method of detecting presence in a sample of a nucleic acid molecule encoding a mammalian 5-oxoprolinase, said method comprising:
   contacting a sample with the DNA oligomer of claim 17, wherein said DNA oligomer hybridizes to a nucleic acid molecule encoding a mammalian 5-oxoprolinase present in said sample, forming a complex therewith; and
   detecting said complex, thereby detecting presence in said sample of a nucleic acid molecule encoding a mammalian 5-oxoprolinase.

19. The method of claim 18 wherein said DNA oligomer is labeled with a detectable marker.

20. A plasmid designated pROPASE and deposited with the American Type Culture Collection under Accession No. 98272.

21. An NdeI/SalI restriction fragment of about 4.0 kb from the plasmid designated pROPASE.

22. The isolated nucleic acid molecule of claim 1, wherein said nucleic acid molecule has a nucleotide sequence which hybridizes to the nucleotide sequence according to SEQ. ID. No. 5 under stringency conditions of 5×SSPE and 50 percent formamide at 42° C. and remains hybridized after washing with 0.5×SSPE at 50 to 65° C.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:1:

```
Ile Gln Thr Gly Pro Pro His Val Glu Lys
1               5                   10
```

(2) INFORMATION FOR SEQ ID NO:2:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:2:

```
Leu Val Gln Gly Gly Val Phe Gln Glu Glu Ala Val Thr Glu Ala Leu
1               5                   10                  15

Arg Ala Pro Gly Lys
            20
```

(2) INFORMATION FOR SEQ ID NO:3:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

```
Ala Cys Ser Gly Thr Asn Asn Leu His Asp Asn Ser Asp Leu Arg Ala
1               5                   10                  15

Gln Val Ala Ala Asn Gln Lys
            20
```

(2) INFORMATION FOR SEQ ID NO:4:

(i) SEQUENCE CHARACTERISTICS:
        (A) LENGTH: 8 amino acids
        (B) TYPE: amino acid

```
        (C) STRANDEDNESS: Not Relevant
        (D) TOPOLOGY: linear (ii) MOLECULE TYPE: peptide (xi) SEQUENCE DESCRIPTION: SEQ ID NO:4:

Arg Thr Val Asn Leu Gly Gly Lys
1               5

(2) INFORMATION FOR SEQ ID NO:5:

(i) SEQUENCE CHARACTERISTICS:
        (A) LENGTH: 3867 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

ATGGGCAGCC CAGAAGGGCG CTTCCATTTC GCCATCGACC GCGGTGGCAC CTTCACAGAT      60

GTCTTTGCCC AGTGCCCTGG AGGGCATGTG CGTGTCCTGA AGCTGCTCTC AGAGGACCCT     120

GCCAACTATC CAGATGCACC CACAGAGGGC ATCCGCCGAA TTCTAGAGCA GGAGGAGGGT     180

GTGCTGCTGC CTCGAGGCCG ACCGCTAGAC ACCAGTCGCA TTGCCAGCAT CCGCATGGGT     240

ACCACGGTGG CCACCAATGC ACTGTTGGAA CGACAGGGAG AACGGGTGGC ACTGCTGGTG     300

ACTCGGGGTT TCCGAGACCT GCTGCATATT GGCACTCAGG CCCGCCCGGA CCTCTTTGAC     360

TTGGCTGTGC CCATGCCAGA GGTTCTGTAT GAGGAAGTGC TGGAGGTAGA TGAGCGAGTG     420

GTGCTGTATC GCGGAGAACC AGGTGCCGGC TCTCCTGTCA AAGGCCGCAC AGGGGACCTG     480

CTAGAGATAC AGCAGCCTGT GGACCTGGAA GCCCTGCGTG GAAGCTGGA GGGGCTCTTG      540

TCTCGGGGCA TTCACAGTCT GGCAGTGGTG CTCATGCATT CGTACACGTG GCCCAGCAT      600

GAGCAGCAGG TGGGCACGCT GGCCCGGGAG CTGGGCTTCA CGCACGTCTC CTTGTCCTCG     660

GAAGTCATGC CCATGGTACG AATTGTTCCT CGGGGCCATA CAGCCTGTGC TGACGCTTAC     720

CTTACTCCCA CCATCCAGCG CTATGTGCAG GGCTTCCGCC GAGGCTTCCA GGGCCAGCTA     780

AAGAATGTGC AAGTTCTCTT CATGCGCTCT GATGGTGGCC TCGCACCCAT GGATGCTTTC     840

AGTGGTTCCC GGGCTGTGCT CTCTGGCCCT GCTGGGGGTG TGGTTGGCTA CTCAGCTACC     900

ACCTACCATC TGGAAGGCGG TCAGCCTGTC ATTGGCTTTG ACATGGGAGG CACATCCACA     960

GACGTGAGCC GCTATGCTGG AGAATTTGAG CATGTCTTTG AGGCTAGCAC AGCAGGCGTT    1020

ACCCTTCAGG CACCCCAGTT GGACATCAAC ACAGTGGCAG CTGGCGGGGG TTCCCGCCTC    1080

TTCTTCAGAT CTGGCCTCTT TGTGGTTGGT CCAGAGTCAG CAGGTGCCCA CCCAGGTCCT    1140

GCCTGCTACC GTAAAGGGGG TCCTGTGACA GTGACAGATG CTAATCTGGT CCTGGGTCGC    1200

CTGCTGCCTG CCTCCTTCCC CTGCATTTTT GGGCCAGGAA AGACCAGCC ACTGTCTCCT     1260

GAGGCTTCCC GAAAGGCTCT AGAGGCTGTG GCCATGGAGG TCAACAGTTT CTTGACCAAT    1320

GGACCGTGCC CAGCTTCCCA ACTAAGTCTG AAGAGGTGG CCATGGGGTT TGTGCGTGTT     1380

GCCAATGAAG CCATGTGCCG GCCTATCCGT GCCCTCACAC AGGCACGAGG CCATGACCCC    1440

TCAGCCCATG TATTGGCTTG CTTTGGAGGA CTGGTGGGC AACACGCTTG TGCCATTGCC     1500

CGGGCCCTGG GGATGGATAC TGTGCACATT CACAGGCACA GCGGGCTGCT GTCAGCACTA    1560

GGACTGGCCT TGGCAGATGT GGTTCACGAA GCACAGGAGC CCTGTTCCCT GTCTTACACA    1620

CCTGAAACCT TTGCACAACT GGACCAGAGA CTGAGCCGCC TGGAGGAGCA GTGTGTGGAT    1680
```

```
GCCTTGCAGG TCCAGGGCTT CCCTAGGTCT CAGATCAGCA CCGAGAGCTT CCTGCATCTT     1740

CGCTACCAAG GCACTGACTG CGCCCTAATG GTGTCTGCCC ATCAGCATCC GGCCACAGCC     1800

TGCTCACCCC GAGCTGGTGA CTTTGGAGCC GCATTTGTGG AGAGGTACAT GAGAGAGTTT     1860

GGCTTCATTA TCCCCGAGCG GCCGGTGGTG GTAGATGATG TACGTGTGAG GGAACTGGC     1920

CGTAGTGGAC TTCAGCTGGA GGACACCCCC AAAATCCAGA CTGGACCTCC CCACGTGGAA     1980

AAGGTGACCC AGTGCTACTT TGAAGGGGGT TATCAGGAGA CTCCCGTGTA CCTTTTAGGA     2040

GAACTAGGCT ACGGGCACCA GCTCCAAGGG CCCTGCCTTA TCATCGACAA CAACAGCACC     2100

ATCCTTGTAG AACCGGGTTG CCAAGCAGAG GTGACTGATA CAGGGGACAT CCGCATTTCT     2160

GTGGGAGCTG AGGGTCCTAG TATGGCAGAT ACCAGGCTTG ACCCCATCCA GCTGTCTATT     2220

TTCTCACACC GCTTCATGAG CATTGCTGAG CAGATGGGCC GCATCCTACA GCGCACAGCC     2280

ATCTCTACCA ACATCAAGGA ACGCCTCGAC TTCTCCTGTG CCCTCTTTGG GCCAGATGGG     2340

GGCCTCGTCT CCAATGCTCC CCACATTCCT GTGCACCTGG GTGCCATGCA AGAGACTGTA     2400

CAGTTCCAGA TTCAGCACTT AGGAGCCGAC CTCCATCCTG GTGATGTGTT GCTCAGCAAC     2460

CATCCCAGCG CAGGGGGCAG CCATCTTCCT GACCTGACTG TCATTACACC GGTGTTTTGG     2520

CCAGGCCAGA CGAGGCCTGT GTTCTACGTG GCTAGCCGAG GCACCACGC AGACATTGGA     2580

GGAATCACAC CGGGCTCTAT GCCGCCTCAC TCCACCACGC TGCAACAGGA GGGTGCCGTT     2640

TTTCTGTCCT TCAAACTGGT CCAGGGAGGC GTCTTCCAGG AAGAGGCAGT GACAGAGGCC     2700

CTACGGGCAC CAGGCAAGAT CTCTGGCTGT AGTGGAACCA GGAACCTGCA TGACAACCTG     2760

TCGGATCTTC GTGCCCAGGT GGCAGCTAAC CAGAAAGGCA TCCAGCTGGT GGGAGAGCTG     2820

ATCGGACAGT ATGGCTTAGA TGTGGTGCAG GCCTATATGG CCATATTCA GGCGAATGCT     2880

GAGCTAGCAG TGAGAGACAT GCTCCGGGCT TTTGGAACTT CCCGGCAGGC CAGGGGCCTG     2940

CCCCTGGAGG TGTCTGCAGA GGATCACATG GATGATGGCC CTCCCATCTG TCTGCGTGTT     3000

CAGATCAACC TGAGTCAGGG CAGTGCGGTA TTTGACTTTA CTGGTTCCGG GTCTGAGGTG     3060

TTTGGCAATC TCAATGCCCC GAGAGCCATA ACACTGTCTG CTCTCATCTA TTGCTTACGC     3120

TGTCTAGTGG GCCGTGACAT CCCACTTAAC CAGGGTTGCC TGGCTCCTGT GCGTGTCATA     3180

ATTCCCAAAG GCTCCATATT GGATCCATCC CCAGAGGCAG CAGTGGTCGG CGGCAACGTG     3240

CTCACATCTC AGCGAGTAGT GGATGTCATT CTGGGGGCTT TTGGGGCCTG TTCAGCCTCC     3300

CAGGGCTGCA TGAACAATGT GACCCTGGGC AATGCCCGTA TGGGCTACTA TGAGACAGTG     3360

GCTGGTGGTG CCGGTGCGGG CCCTGGCTGG CATGGGCGCA GTGGTGTACA CAGTCACATG     3420

ACCAACACAC GCATTACGGA TCCAGAGATT CTGGAGAGTC GGTATCCAGT TATCCTGCGC     3480

CGCTTTGAGC TGAGGCCAGG CTCCGGGGGC CGAGGTCGCT TCCGGGGAGG TGATGGCGTA     3540

GTCCGAGAGC TGGTCTTTCG GGAAGAGGCG CTGTTGTCTG TGCTCACCGA GCGCCGGGCC     3600

TTCCAGCCTT ACGGCCTCCA CGGGGGAGAG CCTGGTGCGC GTGGCTTAAA CCTCCTGATC     3660

AGAAAAGATG GGCGCACAGT GAATTTGGGC GGCAAGACAT CTGTGACCGT GTACCCCGGG     3720

GACGTGTTCT GCCTCCACAC GCCTGGGGGT GGGGCTACG GAGACCCGGA GGATCCAGCG     3780

CCACCACCAG GCTCGCCCCC GCTATTTCCA GCCTTCCCCG AGCGCGGCAG TGTATTCGAG     3840

TACCGCCGCG CCCAGGAAGC CGTATGA                                         3867

(2) INFORMATION FOR SEQ ID NO:6:

(i) SEQUENCE CHARACTERISTICS:
        (A) LENGTH: 1288 amino acids
```

(B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

Met Gly Ser Pro Glu Gly Arg Phe His Phe Ala Ile Asp Arg Gly Gly
1               5                   10                  15

Thr Phe Thr Asp Val Phe Ala Gln Cys Pro Gly Gly His Val Arg Val
                20                  25                  30

Leu Lys Leu Leu Ser Glu Asp Pro Ala Asn Tyr Pro Asp Ala Pro Thr
            35                  40                  45

Glu Gly Ile Arg Arg Ile Leu Glu Gln Glu Gly Val Leu Leu Pro
50                      55                  60

Arg Gly Arg Pro Leu Asp Thr Ser Arg Ile Ala Ser Ile Arg Met Gly
65                  70                  75                  80

Thr Thr Val Ala Thr Asn Ala Leu Leu Glu Arg Gln Gly Glu Arg Val
                85                  90                  95

Ala Leu Leu Val Thr Arg Gly Phe Arg Asp Leu Leu His Ile Gly Thr
                100                 105                 110

Gln Ala Arg Pro Asp Leu Phe Asp Leu Ala Val Pro Met Pro Glu Val
            115                 120                 125

Leu Tyr Glu Glu Val Leu Glu Val Asp Glu Arg Val Val Leu Tyr Arg
130                 135                 140

Gly Glu Pro Gly Ala Gly Ser Pro Val Lys Gly Arg Thr Gly Asp Leu
145                 150                 155                 160

Leu Glu Ile Gln Gln Pro Val Asp Leu Glu Ala Leu Arg Gly Lys Leu
                165                 170                 175

Glu Gly Leu Leu Ser Arg Gly Ile His Ser Leu Ala Val Val Leu Met
            180                 185                 190

His Ser Tyr Thr Trp Ala Gln His Glu Gln Gln Val Gly Thr Leu Ala
        195                 200                 205

Arg Glu Leu Gly Phe Thr His Val Ser Leu Ser Ser Glu Val Met Pro
210                 215                 220

Met Val Arg Ile Val Pro Arg Gly His Thr Ala Cys Ala Asp Ala Tyr
225                 230                 235                 240

Leu Thr Pro Thr Ile Gln Arg Tyr Val Gln Gly Phe Arg Arg Gly Phe
                245                 250                 255

Gln Gly Gln Leu Lys Asn Val Gln Val Leu Phe Met Arg Ser Asp Gly
            260                 265                 270

Gly Leu Ala Pro Met Asp Ala Phe Ser Gly Ser Arg Ala Val Leu Ser
275                 280                 285

Gly Pro Ala Gly Val Val Gly Tyr Ser Ala Thr Thr Tyr His Leu
290                 295                 300

Glu Gly Gly Gln Pro Val Ile Gly Phe Asp Met Gly Gly Thr Ser Thr
305                 310                 315                 320

Asp Val Ser Arg Tyr Ala Gly Glu Phe Glu His Val Phe Glu Ala Ser
                325                 330                 335

Thr Ala Gly Val Thr Leu Gln Ala Pro Gln Leu Asp Ile Asn Thr Val
            340                 345                 350

Ala Ala Gly Gly Gly Ser Arg Leu Phe Phe Arg Ser Gly Leu Phe Val
            355                 360                 365

Val Gly Pro Glu Ser Ala Gly Ala His Pro Gly Pro Ala Cys Tyr Arg
370                 375                 380

```
Lys Gly Gly Pro Val Thr Val Thr Asp Ala Asn Leu Val Leu Gly Arg
385                 390                 395                 400

Leu Leu Pro Ala Ser Phe Pro Cys Ile Phe Gly Pro Gly Glu Asp Gln
            405                 410                 415

Pro Leu Ser Pro Glu Ala Ser Arg Lys Ala Leu Glu Ala Val Ala Met
            420                 425                 430

Glu Val Asn Ser Phe Leu Thr Asn Gly Pro Cys Pro Ala Ser Gln Leu
            435                 440                 445

Ser Leu Glu Glu Val Ala Met Gly Phe Val Arg Val Ala Asn Glu Ala
    450                 455                 460

Met Cys Arg Pro Ile Arg Ala Leu Thr Gln Ala Arg Gly His Asp Pro
465                 470                 475                 480

Ser Ala His Val Leu Ala Cys Phe Gly Gly Ala Gly Gly Gln His Ala
                485                 490                 495

Cys Ala Ile Ala Arg Ala Leu Gly Met Asp Thr Val His Ile His Arg
                500                 505                 510

His Ser Gly Leu Leu Ser Ala Leu Gly Leu Ala Leu Ala Asp Val Val
            515                 520                 525

His Glu Ala Gln Glu Pro Cys Ser Leu Ser Tyr Thr Pro Glu Thr Phe
    530                 535                 540

Ala Gln Leu Asp Gln Arg Leu Ser Arg Leu Glu Glu Gln Cys Val Asp
545                 550                 555                 560

Ala Leu Gln Val Gln Gly Phe Pro Arg Ser Gln Ile Ser Thr Glu Ser
                565                 570                 575

Phe Leu His Leu Arg Tyr Gln Gly Thr Asp Cys Ala Leu Met Val Ser
            580                 585                 590

Ala His Gln His Pro Ala Thr Ala Cys Ser Pro Arg Ala Gly Asp Phe
    595                 600                 605

Gly Ala Ala Phe Val Glu Arg Tyr Met Arg Glu Phe Gly Phe Ile Ile
            610                 615                 620

Pro Glu Arg Pro Val Val Val Asp Asp Val Arg Val Arg Gly Thr Gly
625                 630                 635                 640

Arg Ser Gly Leu Gln Leu Glu Asp Thr Pro Lys Ile Gln Thr Gly Pro
                645                 650                 655

Pro His Val Glu Lys Val Thr Gln Cys Tyr Phe Glu Gly Gly Tyr Gln
            660                 665                 670

Glu Thr Pro Val Tyr Leu Leu Gly Glu Leu Gly Tyr Gly His Gln Leu
            675                 680                 685

Gln Gly Pro Cys Leu Ile Ile Asp Asn Asn Ser Thr Ile Leu Val Glu
    690                 695                 700

Pro Gly Cys Gln Ala Glu Val Thr Asp Thr Gly Asp Ile Arg Ile Ser
705                 710                 715                 720

Val Gly Ala Glu Gly Pro Ser Met Ala Asp Thr Arg Leu Asp Pro Ile
                725                 730                 735

Gln Leu Ser Ile Phe Ser His Arg Phe Met Ser Ile Ala Glu Gln Met
            740                 745                 750

Gly Arg Ile Leu Gln Arg Thr Ala Ile Ser Thr Asn Ile Lys Glu Arg
            755                 760                 765

Leu Asp Phe Ser Cys Ala Leu Phe Gly Pro Asp Gly Gly Leu Val Ser
    770                 775                 780

Asn Ala Pro His Ile Pro Val His Leu Gly Ala Met Gln Glu Thr Val
785                 790                 795                 800
```

```
Gln Phe Gln Ile Gln His Leu Gly Ala Asp Leu His Pro Gly Asp Val
                805                 810                 815

Leu Leu Ser Asn His Pro Ser Ala Gly Gly Ser His Leu Pro Asp Leu
            820                 825                 830

Thr Val Ile Thr Pro Val Phe Trp Pro Gly Gln Thr Arg Pro Val Phe
            835                 840                 845

Tyr Val Ala Ser Arg Gly His His Ala Asp Ile Gly Gly Ile Thr Pro
850                 855                 860

Gly Ser Met Pro Pro His Ser Thr Thr Leu Gln Gln Glu Gly Ala Val
865                 870                 875                 880

Phe Leu Ser Phe Lys Leu Val Gln Gly Gly Val Phe Gln Glu Glu Ala
            885                 890                 895

Val Thr Glu Ala Leu Arg Ala Pro Gly Lys Ile Ser Gly Cys Ser Gly
            900                 905                 910

Thr Arg Asn Leu His Asp Asn Leu Ser Asp Leu Arg Ala Gln Val Ala
            915                 920                 925

Ala Asn Gln Lys Gly Ile Gln Leu Val Gly Glu Leu Ile Gly Gln Tyr
            930                 935                 940

Gly Leu Asp Val Val Gln Ala Tyr Met Gly His Ile Gln Ala Asn Ala
945                 950                 955                 960

Glu Leu Ala Val Arg Asp Met Leu Arg Ala Phe Gly Thr Ser Arg Gln
            965                 970                 975

Ala Arg Gly Leu Pro Leu Glu Val Ser Ala Glu Asp His Met Asp Asp
            980                 985                 990

Gly Ser Pro Ile Cys Leu Arg Val Gln Ile Asn Leu Ser Gln Gly Ser
            995                 1000                1005

Ala Val Phe Asp Phe Thr Gly Ser Gly Ser Glu Val Phe Gly Asn Leu
            1010                1015                1020

Asn Ala Pro Arg Ala Ile Thr Leu Ser Ala Leu Ile Tyr Cys Leu Arg
1025                1030                1035                1040

Cys Leu Val Gly Arg Asp Ile Pro Leu Asn Gln Gly Cys Leu Ala Pro
            1045                1050                1055

Val Arg Val Ile Ile Pro Lys Gly Ser Ile Leu Asp Pro Ser Pro Glu
            1060                1065                1070

Ala Ala Val Val Gly Gly Asn Val Leu Thr Ser Gln Arg Val Val Asp
            1075                1080                1085

Val Ile Leu Gly Ala Phe Gly Ala Cys Ser Ala Ser Gln Gly Cys Met
            1090                1095                1100

Asn Asn Val Thr Leu Gly Asn Ala Arg Met Gly Tyr Tyr Glu Thr Val
1105                1110                1115                1120

Ala Gly Gly Ala Gly Ala Gly Pro Gly Trp His Gly Arg Ser Gly Val
            1125                1130                1135

His Ser His Met Thr Asn Thr Arg Ile Thr Asp Pro Glu Ile Leu Glu
            1140                1145                1150

Ser Arg Tyr Pro Val Ile Leu Arg Arg Phe Glu Leu Arg Pro Gly Ser
            1155                1160                1165

Gly Gly Arg Gly Arg Phe Arg Gly Gly Asp Gly Val Val Arg Glu Leu
            1170                1175                1180

Val Phe Arg Glu Glu Ala Leu Leu Ser Val Leu Thr Glu Arg Arg Ala
1185                1190                1195                1200

Phe Gln Pro Tyr Gly Leu His Gly Gly Glu Pro Gly Ala Arg Gly Leu
            1205                1210                1215

Asn Leu Leu Ile Arg Lys Asp Gly Arg Thr Val Asn Leu Gly Gly Lys
```

```
                    1220          1225          1230
Thr Ser Val Thr Val Tyr Pro Gly Asp Val Phe Cys Leu His Thr Pro
            1235          1240          1245

Gly Gly Gly Gly Tyr Gly Asp Pro Glu Asp Pro Ala Pro Pro Gly
            1250          1255          1260

Ser Pro Pro Leu Phe Pro Ala Phe Pro Glu Arg Gly Ser Val Phe Glu
1265          1270          1275          1280

Tyr Arg Arg Ala Gln Glu Ala Val
            1285
```

(2) INFORMATION FOR SEQ ID NO:7:

(i) SEQUENCE CHARACTERISTICS:
        (A) LENGTH: 4016 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
AGCACATTCA CCCTCTGAGG CAAGTCGCCG GCCTTTTCAG CGTTTTTTGC TGTTCTCCCA    60
GGGTTACCAG CTGAAGAGCC ATTCCTGGAC TCCAGCTTCA ACGTCATGGG CAGCCCAGAA   120
GGGCGCTTCC ATTTCGCCAT CGACCGCGGT GGCACCTTCA CAGATGTCTT TGCCCAGTGC   180
CCTGGAGGGC ATGTGCGTGT CCTGAAGCTG CTCTCAGAGG ACCCTGCCAA CTATCCAGAT   240
GCACCCACAG AGGGCATCCG CCGAATTCTA GAGCAGGAGG AGGGTGTGCT GCTGCCTCGA   300
GGCCGACCGC TAGACACCAG TCGCATTGCC AGCATCCGCA TGGGTACCAC GGTGGCCACC   360
AATGCACTGT TGGAACGACA GGGAGAACGG GTGGCACTGC TGGTGACTCG GGGTTTCCGA   420
GACCTGCTGC ATATTGGCAC TCAGGCCCGC CCGGACCTCT TTGACTTGGC TGTGCCCATG   480
CCAGAGGTTC TGTATGAGGA AGTGCTGGAG GTAGATGAGC GAGTGGTGCT GTATCGCGGA   540
GAACCAGGTG CCGGCTCTCC TGTCAAAGGC CGCACAGGGG ACCTGCTAGA GATACAGCAG   600
CCTGTGGACC TGGAAGCCCT GCGTGGGAAG CTGGAGGGGC TCTTGTCTCG GGGCATTCAC   660
AGTCTGGCAG TGGTGCTCAT GCATTCGTAC ACGTGGGCCC AGCATGAGCA GCAGGTGGGC   720
ACGCTGGCCC GGGAGCTGGG CTTCACGCAC GTCTCCTTGT CCTCGGAAGT CATGCCCATG   780
GTACGAATTG TTCCTCGGGG CCATACAGCC TGTGCTGACG CTTACCTTAC TCCCACCATC   840
CAGCGCTATG TGCAGGGCTT CCGCCGAGGC TTCCAGGGCC AGCTAAAGAA TGTGCAAGTT   900
CTCTTCATGC GCTCTGATGG TGGCCTCGCA CCCATGGATG CTTTCAGTGG TTCCCGGGCT   960
GTGCTCTCTG GCCCTGCTGG GGGTGTGGTT GGCTACTCAG CTACCACCTA CCATCTGGAA  1020
GGCGGTCAGC CTGTCATTGG CTTTGACATG GGAGGCACAT CCACAGACGT GAGCCGCTAT  1080
GCTGGAGAAT TTGAGCATGT CTTTGAGGCT AGCACAGCAG GCGTTACCCT TCAGGCACCC  1140
CAGTTGGACA TCAACACAGT GGCAGCTGGC GGGGGTTCCC GCCTCTTCTT CAGATCTGGC  1200
CTCTTTGTGG TTGGTCCAGA GTCAGCAGGT GCCCACCCAG GTCCTGCCTG CTACCGTAAA  1260
GGGGGTCCTG TGACAGTGAC AGATGCTAAT CTGGTCCTGG GTCGCCTGCT GCCTGCCTCC  1320
TTCCCCTGCA TTTTTGGGCC AGGAGAAGAC CAGCCACTGT CTCCTGAGGC TTCCCGAAAG  1380
GCTCTAGAGG CTGTGGCCAT GGAGGTCAAC AGTTTCTTGA CCAATGGACC GTGCCCAGCT  1440
TCCCAACTAA GTCTGGAAGA GGTGGCCATG GGGTTTGTGC GTGTTGCCAA TGAAGCCATG  1500
TGCCGGCCTA TCCGTGCCCT CACACAGGCA CGAGGCCATG ACCCCTCAGC CCATGTATTG  1560
```

```
-continued

GCTTGCTTTG GAGGAGCTGG TGGGCAACAC GCTTGTGCCA TTGCCCGGGC CCTGGGGATG    1620

GATACTGTGC ACATTCACAG GCACAGCGGG CTGCTGTCAG CACTAGGACT GGCCTTGGCA    1680

GATGTGGTTC ACGAAGCACA GGAGCCCTGT TCCCTGTCTT ACACACCTGA AACCTTTGCA    1740

CAACTGGACC AGAGACTGAG CCGCCTGGAG GAGCAGTGTG TGGATGCCTT GCAGGTCCAG    1800

GGCTTCCCTA GGTCTCAGAT CAGCACCGAG AGCTTCCTGC ATCTTCGCTA CCAAGGCACT    1860

GACTGCGCCC TAATGGTGTC TGCCCATCAG CATCCGGCCA CAGCCTGCTC ACCCCGAGCT    1920

GGTGACTTTG GAGCCGCATT TGTGGAGAGG TACATGAGAG AGTTTGGCTT CATTATCCCC    1980

GAGCGGCCGG TGGTGGTAGA TGATGTACGT GTGAGGGAA CTGGCCGTAG TGGACTTCAG     2040

CTGGAGGACA CCCCCAAAAT CCAGACTGGA CCTCCCCACG TGGAAAAGGT GACCCAGTGC    2100

TACTTTGAAG GGGGTTATCA GGAGACTCCC GTGTACCTTT TAGGAGAACT AGGCTACGGG    2160

CACCAGCTCC AAGGGCCCTG CCTTATCATC GACAACAACA GCACCATCCT TGTAGAACCG    2220

GGTTGCCAAG CAGAGGTGAC TGATACAGGG GACATCCGCA TTTCTGTGGG AGCTGAGGGT    2280

CCTAGTATGG CAGATACCAG GCTTGACCCC ATCCAGCTGT CTATTTTCTC ACACCGCTTC    2340

ATGAGCATTG CTGAGCAGAT GGGCCGCATC CTACAGCGCA CAGCCATCTC TACCAACATC    2400

AAGGAACGCC TCGACTTCTC CTGTGCCCTC TTTGGGCCAG ATGGGGGCCT CGTCTCCAAT    2460

GCTCCCCACA TTCCTGTGCA CCTGGGTGCC ATGCAAGAGA CTGTACAGTT CCAGATTCAG    2520

CACTTAGGAG CCGACCTCCA TCCTGGTGAT GTGTTGCTCA GCAACCATCC CAGCGCAGGG    2580

GGCAGCCATC TTCCTGACCT GACTGTCATT ACACCGGTGT TTTGGCCAGG CCAGACGAGG    2640

CCTGTGTTCT ACGTGGCTAG CCGAGGGCAC CACGCAGACA TTGGAGGAAT CACACCGGGC    2700

TCTATGCCGC CTCACTCCAC CACGCTGCAA CAGGAGGGTG CCGTTTTTCT GTCCTTCAAA    2760

CTGGTCCAGG GAGGCGTCTT CCAGGAAGAG GCAGTGACAG AGGCCCTACG GGCACCAGGC    2820

AAGATCTCTG GCTGTAGTGG AACCAGGAAC CTGCATGACA ACCTGTCGGA TCTTCGTGCC    2880

CAGGTGGCAG CTAACCAGAA AGGCATCCAG CTGGTGGGAG AGCTGATCGG ACAGTATGGC    2940

TTAGATGTGG TGCAGGCCTA TATGGGCCAT ATTCAGGCGA ATGCTGAGCT AGCAGTGAGA    3000

GACATGCTCC GGGCTTTTGG AACTTCCCGG CAGGCCAGGG GCCTGCCCCT GGAGGTGTCT    3060

GCAGAGGATC ACATGGATGA TGGCTCTCCC ATCTGTCTGC GTGTTCAGAT CAACCTGAGT    3120

CAGGGCAGTG CGGTATTTGA CTTTACTGGT TCCGGGTCTG AGGTGTTTGG CAATCTCAAT    3180

GCCCCGAGAG CCATAACACT GTCTGCTCTC ATCTATTGCT TACGCTGTCT AGTGGGCCGT    3240

GACATCCCAC TTAACCAGGG TTGCCTGGCT CCTGTGCGTG TCATAATTCC CAAAGGCTCC    3300

ATATTGGATC CATCCCCAGA GGCAGCAGTG GTCGGCGGCA ACGTGCTCAC ATCTCAGCGA    3360

GTAGTGGATG TCATTCTGGG GGCTTTTGGG GCCTGTTCAG CCTCCCAGGG CTGCATGAAC    3420

AATGTGACCC TGGGCAATGC CCGTATGGGC TACTATGAGA CAGTGGCTGG TGGTGCCGGT    3480

GCGGGCCCTG GCTGGCATGG GCGCAGTGGT GTACACAGTC ACATGACCAA CACACGCATT    3540

ACGGATCCAG AGATTCTGGA GAGTCGGTAT CCAGTTATCC TGCGCCGCTT TGAGCTGAGG    3600

CCAGGCTCCG GGGCCGAGG TCGCTTCCGG GGAGGTGATG GCGTAGTCCG AGAGCTGGTC     3660

TTTCGGGAAG AGGCGCTGTT GTCTGTGCTC ACCGAGCGCC GGGCCTTCCA GCCTTACGGC    3720

CTCCACGGGG GAGAGCCTGG TGCGCGTGGC TTAAACCTCC TGATCAGAAA AGATGGGCGC    3780

ACAGTGAATT TGGGCGGCAA GACATCTGTG ACCGTGTACC CCGGGGACGT GTTCTGCCTC    3840

CACACGCCTG GGGGTGGGGG CTACGGAGAC CCGGAGGATC CAGCGCCACC ACCAGGCTCG    3900

CCCCCGCTAT TTCCAGCCTT CCCCGAGCGC GGCAGTGTAT TCGAGTACCG CCGCGCCCAG    3960
```

-continued

```
GAAGCCGTAT GAGTGCCCCA CAATAAAGAT CCTTTGAATC GCAAAAAAAA AAAAAA          4016

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GTATTCTCAA GGAAGGAAGG CAGTAACAGA AGGC                                   34

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

Val Phe Gln Glu Glu Ala Val Thr Glu Ala
1               5                   10

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CTCCAGCTTC AACCATATGG GCAGC                                             25
```